(12) United States Patent
Myllyoja et al.

(10) Patent No.: US 7,998,339 B2
(45) Date of Patent: Aug. 16, 2011

(54) PROCESS FOR PRODUCING A HYDROCARBON COMPONENT

(75) Inventors: Jukka Myllyoja, Vantaa (FI); Juha Jakkula, Kerava (FI); Pekka Aalto, Porvoo (FI); Eija Koivusalmi, Kulloonkylä (FI); Johan-Fredrik Selin, Helsinki (FI); Juha Moilanen, Porvoo (FI)

(73) Assignee: Neste Oil Oyj, Espoo (FI)

( * ) Notice: Subject to any disclaimer, the term of this patent is extended or adjusted under 35 U.S.C. 154(b) by 91 days.

(21) Appl. No.: 11/636,567

(22) Filed: Dec. 11, 2006

(65) Prior Publication Data

US 2007/0161832 A1    Jul. 12, 2007

Related U.S. Application Data

(60) Provisional application No. 60/749,036, filed on Dec. 12, 2005.

(51) Int. Cl.
*C10M 101/04* (2006.01)
*C10M 105/22* (2006.01)
*C10M 105/32* (2006.01)

(52) U.S. Cl. ............... 208/18; 508/216; 585/7; 585/16; 585/240

(58) Field of Classification Search ............ 208/18, 208/19; 585/7, 240, 16; 508/216, 217
See application file for complete search history.

(56) References Cited

U.S. PATENT DOCUMENTS

| | | |
|---|---|---|
| 3,182,017 A | 5/1965 | Fleck et al. |
| 3,242,080 A | 3/1966 | Wiley et al. |
| 3,444,143 A | 5/1969 | Morris et al. |
| 3,501,546 A | 3/1970 | Dubeck et al. |
| 4,026,960 A | 5/1977 | Nishida et al. |
| 4,133,841 A | 1/1979 | Cosyns et al. |
| 4,299,979 A | 11/1981 | Murphy |
| 4,317,948 A | 3/1982 | Heckelsberg |
| 4,457,944 A | 7/1984 | Conrad et al. |
| 4,744,884 A | 5/1988 | Moorehead et al. |
| 4,783,274 A | 11/1988 | Jokinen et al. |
| 5,333,698 A | 8/1994 | Van Slyke |
| 5,416,239 A | 5/1995 | Westfechtel et al. |
| 5,444,170 A | 8/1995 | Vedage |
| 5,516,960 A | 5/1996 | Robinson |
| 5,705,722 A | 1/1998 | Monnier et al. |

(Continued)

FOREIGN PATENT DOCUMENTS

DE    1024238 B    2/1958

(Continued)

OTHER PUBLICATIONS

Fette, Seifen, Anstrichmittel, U.-A. Schaper, vol. 82, No. 11, 1980, pp. 454-456, "Die gemischte Guerbet-Reaktion zwischen cyclischen und acyclischen Alkoholen".

(Continued)

*Primary Examiner* — Walter D Griffin
*Assistant Examiner* — Renee Robinson
(74) *Attorney, Agent, or Firm* — Birch, Stewart, Kolasch and Birch, LLP

(57) ABSTRACT

The invention relates to a process for producing a new type of high-quality hydrocarbon base oil of biological origin. The process of the invention comprises ketonisation, hydrodeoxygenation, and isomerization steps. Fatty acids and/or fatty acid esters based on a biological raw material are preferably used as the feedstock.

37 Claims, 3 Drawing Sheets

U.S. PATENT DOCUMENTS

| | | | |
|---|---|---|---|
| 5,719,097 | A | 2/1998 | Chang et al. |
| 6,245,725 | B1 | 6/2001 | Tanaka et al. |
| 6,562,230 | B1 * | 5/2003 | O'Rear et al. ............ 208/66 |
| 6,599,864 | B1 * | 7/2003 | Bertomeu ............ 508/110 |
| 6,683,224 | B1 | 1/2004 | Hourticolon et al. |
| 6,703,356 | B1 | 3/2004 | Wu |
| 2002/0062055 | A1 | 5/2002 | Raulo et al. |
| 2003/0181769 | A1 | 9/2003 | Both et al. |
| 2004/0002620 | A1 | 1/2004 | Schwerin et al. |
| 2004/0053796 | A1 | 3/2004 | O'Rear |
| 2004/0055209 | A1 | 3/2004 | Jakkula et al. |
| 2004/0099571 | A1 * | 5/2004 | Germaine et al. ........ 208/108 |
| 2004/0230085 | A1 | 11/2004 | Jakkula et al. |
| 2005/0077209 | A1 * | 4/2005 | Miller et al. ............ 208/96 |
| 2005/0133408 | A1 * | 6/2005 | Abernathy et al. ......... 208/19 |
| 2005/0241990 | A1 * | 11/2005 | Ziemer et al. ............ 208/19 |
| 2006/0027486 | A1 | 2/2006 | Rosenbaum et al. |

FOREIGN PATENT DOCUMENTS

| | | |
|---|---|---|
| DE | 33407111 | 10/1983 |
| EP | 0 209 997 A1 | 1/1987 |
| EP | 0239320 | 9/1987 |
| EP | 0 591 297 | 4/1994 |
| EP | 0 457 665 B1 | 11/1994 |
| EP | 0 774 451 | 5/1997 |
| EP | 1396531 A2 | 3/2004 |
| EP | 1681337 A1 | 7/2006 |
| FI | 66899 B | 8/1984 |
| FI | 100248 | 10/1997 |
| FR | 579 601 | 10/1924 |
| GB | 175974 A | 6/1923 |
| GB | 1193220 A | 5/1970 |
| GB | 1 524 781 | 9/1978 |
| JP | 59108008 A | 6/1984 |
| JP | 01066792 A | 3/1989 |
| WO | WO-93/00320 A1 | 1/1993 |
| WO | WO-96/17902 A1 | 6/1996 |
| WO | WO-2004/062763 A2 | 7/2004 |

OTHER PUBLICATIONS

Ullmanns Encyklopadie der technischen Chemie, 4., neubearbeitete und erweiterte Auflage, Band 13, Verlag Chemie GmbH, Weinheim 1983, Hydrierung p. 140.

Klimkiewicz et al., "Ketonization of long chain esters from transesterification of technical waste fats," J. Chem. Technol. Biotechnol., vol. 76, 2001, pp. 35-38.

English translation of Finnish Patent Office Search Report for Finnish Patent Application No. FI-200556665.

PCT Notification of Transmittal of the International Search Report and the Written Opinion of the International Searching Authority or the Declaration of Application No. FI-2005050550.

Ulmanns, Encykolpadie der technischen Chemie, 4., neubearbeitete und erweiterte Auflage, Band 13, (1976), Verlag Chemie GmbH, Weinheim, p. 146.

Office Action issued in U.S. Appl. No. 11/637,159 on Aug. 19, 2010.

U.S. Notice of Allowance dated Feb. 23, 2011 issued in U.S. Appl. No. 12/433,394.

Office Action issued in U.S. Appl. No. 11/637,139 on Jan. 23, 2009.
Office Action issues in U.S. Appl. No. 11/637,159 on Jul. 1, 2010.
Office Action issued in U.S. Appl. No. 11/637,159 on Nov. 19, 2009.
Burg, et al., JAOCS, (1991), vol. 68, (8), pp. 600-603.
Cui, S,T., et al., "Nonequlibrium Molecular Dynamics Simulation of the Rheology of Linear and Branched Alkanes", International Journal of Thermophysics, 1988, vol. 19, No. 2, pp. 449-459.
Kirk-Othmer, Encyclopedia of Chemical Technology, 3rd ed., (1980), vol. 7, Wiley, p. 768.
Koster, R.M., et al., Active sites in the clay catalysed dimerisation of oleic acid, Journal of Molecular Catalysis A: Chemical, (1998), vol. 134, pp. 159-169.
Laurent, E., et al., Study of the hydrodeoygenation of carbonyl, carboxylic and guaiacyl groups over sulfided CoMo/ $\gamma$-Al2O3 and NiMo/ $\gamma$-Al2O3 catalyst. II. Influence of Water, ammonia and hydrogen sulfide, Applied Catalysis A, (1994), vol. 109. pp. 97-115.
Laurent, E., et al., Study of hydrodeoygenation of carbonyl, carboxylic and guaiacyl groups over sulfided CoMo/ $\gamma$-Al2O3 and NiMo/ $\gamma$-Al2O3 catalyst. I. Catalytic reaction schemes, Applied Catalysus A, (1994), vol. 109, pp. 77-96.
Maier, W.F. et al., Gas Phase Decarboxylation of Carboxylic Acids, Chem. Ber., (1982), vol. 115, pp. 808-812.
Morrison, R.T. and Boyd, R. N., Organic Chemistry, 5th ed. (1987), Allyn and Bacon, Newton, Massachusetts, pp. 94, 640, 679-680, 913-914.
Notification of Transmittal of the International Search Report and Written Opinion of the International Searching Authority for PCT/FI2006/050553.
"Scope of Accreditation for Testing" Thai Laboratory Accreditation Scheme, Thai Industrial Standards Industry, Ministry of Industry, Issue No. 9, Sep. 25, 2009.
Translation of Search Report of FI-20055661 dated May 12, 2006.
Office Action issued in U.S. Appl. No. 11/637,139 on Apr. 6, 2009.
Office Action issued in U.S. Appl. No. 11/637,107 on Apr. 6, 2009.
Office Action issued in U.S. Appl. No. 11/637,107 on Dec. 14, 2009.
Office Action issued in U.S. Appl. No. 11/637,159 on Mar. 11, 2009.
Search report from PCT/FI2006/050548 dated Apr. 12, 2007.
Kirk-Othmer, Encyclopedia of Chemical Technology, 3rd ed., (1980), vol. 9, Wiley, p. 370.
Office Action issued in U.S. Appl. No. 11/637,139 on Dec. 31, 2009.
Office Action issued in U.S. Appl. No. 11/637,107 on Apr. 21, 2010.
Office Action dated Aug. 6, 2010 issued in U.S. Appl. No. 11/637,107.
Office Action dated Aug. 25, 2010 issued in U.S. Appl. No. 12/433,394.
US Notice of Allowance dated Jul. 1, 2010 issued in U.S. Appl. No. 11/637,159.
US Notice of Allowance dated Aug. 13, 2010 issued in U.S. Appl. No. 11/637,139.
US Office Action dated Apr. 26, 2010 issued in U.S. Appl. No. 11/637,139.
US Notice of Allowance dated Sep. 30, 2010 issued in U.S. Appl. No. 11/637,159.
Office Action issued in U.S. Appl. No. 11/637,107 on Mar. 31, 2011.

* cited by examiner

PROCESS FOR PRODUCING A HYDROCARBON COMPONENT

This Nonprovisional application claims priority under 35 U.S.C. §119(e) on U.S. Provisional Application No. 60/749,036 filed on Dec. 12, 2005, the entire contents of which are hereby incorporated by reference.

TECHNICAL FIELD

The invention relates to a process for producing a hydrocarbon component, and particularly a process for producing a high-quality branched saturated hydrocarbon component of biological origin to be used as a new kind of base oil. The process comprising ketonisation, hydrodeoxygenation, and isomerization steps utilizes as feedstock raw material of biological origin eventually derived from plant oils, animal fats, natural waxes, and carbohydrates. Also corresponding synthetic materials and combinations thereof may be used as feedstock.

STATE OF THE ART

Base oils are commonly used for the production of lubricants, such as lubricating oils for automotives, industrial lubricants and lubricating greases. They are also used as process oils, white oils and metal working oils. Finished lubricants consist of two general components, lubricating base oil and additives. Lubricating base oil is the major constituent in these finished lubricants and contributes significantly to the properties of the finished lubricant. In general, a few lubricating base oils are used to manufacture a wide variety of finished lubricants by varying the mixtures of individual lubricating base oils and individual additives.

Base oils according to the classification of the American Petroleum Institute (API) Group III or IV are used in high-quality lubricants. API base oil classification is shown in Table 1.

TABLE 1

API base oil classification

| Group | Saturated hydrocarbons, wt-% (ASTM D 2007) | Sulfur, wt-% (ASTM D 1552/D 2622/D 3120/ D4294/D 4927) | Viscosity index (VI) (ASTM D 2270) |
|---|---|---|---|
| I | <90 and/or | >0.03 | 80 ≦ VI < 120 |
| II | ≧90 | ≦0.03 | 80 ≦ VI < 120 |
| III | ≧90 | ≦0.03 | ≧120 |
| IV | All polyalphaolefins (PAO) | | |
| V | All other base oils not belonging to Groups I-IV | | |

Oils of the Group III are base oils with very high viscosity indices (VHVI) produced by modern methods from crude oil by hydrocracking, followed by isomerization of the waxy linear paraffins to give branched paraffins. Oils of Group III also include base oils produced from Slack Wax paraffins from mineral oils, and from waxes obtained by Fischer-Tropsch synthesis (GTL waxes) for instance from coal or natural gas using corresponding isomerization techniques. Oils of Group IV are synthetic polyalpha-olefins (PAO). A similar classification is also used by ATIEL (Association Technique de l'Industrie Européenne des Lubrifiants, or Technical Association of the European Lubricants Industry), said classification also comprising Group VI: Polyintemalolefins (PIO). In addition to the official classification, also Group II+ is commonly used in this field, this group comprising saturated and non-sulfurous base oils having viscosity indices of more than 110, but below 120. In these classifications saturated hydrocarbons include paraffinic and naphthenic compounds, but not aromatics.

There is also available a definition for base stocks according to API 1509 as: "A base stock is a lubricant component that is produced by a single manufacturer to the same specifications (independent of feed source or manufacturer's location); that meets the same manufacturer's specification; and that is identified by a unique formula, product identification number, or both. Base stocks may be manufactured using a variety of different processes." Base oil is the base stock or blend of base stocks used in API-licensed oil. The known base stock types are 1) Mineral oil (paraffinic, naphthenic, aromatic), 2) Synthetic (polyalphaolefins, alkylated aromatics, diesters, polyol esters, polyalkylene glycols, phosphate esters, silicones), and 3) Plant oil.

Already for a long time, especially the automotive industry has required lubricants and thus base oils with improved technical properties. Increasingly, the specifications for finished lubricants require products with excellent low temperature properties, high oxidation stability and low volatility. Generally lubricating base oils are base oils having kinematic viscosity of about 3 cSt or greater at 100° C. (KV100); a pour point (PP) of about −12° C. or less; and a viscosity index (VI) about 120 or greater. In addition to low pour points also the low-temperature fluidity of multi-grade engine oils is needed to guarantee that in cold weather the engine starts easily. The low-temperature fluidity is demonstrated as apparent viscosity in cold cranking simulator (CCS) tests at −5 to −40° C. temperature. Lubricating base oils having KV100 of about 4 cSt should typically have CCS viscosity at −30° C. (CCS-30) lower than 1800 cP and oils having KV100 of about 5 cSt should have CCS-30 lower than 2700 cP. The lower the value is the better. In general, lubricating base oils should have Noack volatility no greater than current conventional Group I or Group II light neutral oils. Currently, only a small fraction of the base oils manufactured today can be used in formulations to meet the latest, most demanding lubricant specifications.

It is no longer possible to produce lubricants complying with the specifications of the most demanding car manufacturers, from conventional mineral oils. Typically, mineral oils often contain too high concentrations of aromatic, sulfur, and nitrogen compounds, and further, they also have a high volatility and a modest viscosity index, that is, viscosity-temperature dependence. Moreover, response of mineral oils to antioxidant additives is often low. Synthetic and so-called semi-synthetic base oils play an increasingly important role especially in automotive lubricants, such as in engine and gear oils. A similar development can be seen for industrial lubricants. Service life of lubricants is desirably as long as possible, thus avoiding frequent oil changes by the user, and further allowing extended maintenance intervals of vehicles for instance in commercial transportation. In the past decade, engine oil change intervals for passenger cars have increased five fold, being at best 50,000 km. For heavy-duty vehicles, engine oil change intervals are at present already on the level of 100,000 km.

The production of lubricants is influenced by increasingly common "Life Cycle Approach" (LCA) concerning environment, health and safety factors of the product. What is aimed with LCA are an extended service life of the product, and minimal drawbacks to the environments associated with the production, use, handling and disposal of the product. Longer oil change intervals of high-quality base oils result in decreased consumption of non-renewable mineral crude oil based raw materials, and lower amounts of hazardous waste oil products.

In addition to the demands for engine technology and base oil production, also strict environmental requirements direct the industry to develop more sophisticated base oils. Sulfur free fuels and base oils are required in order to gain full effect of new and efficient anti-pollution technologies in modern vehicles and to cut emissions of nitrogen oxides, volatile hydrocarbons and particles, as well as to achieve direct reduction of sulfur dioxide in exhaust gases. The European Union has decided that these fuels shall be available to the market from 2005 and they must be the only form on sale from 2009. Conventional mineral oil base oils contain sulfur, nitrogen, aromatic compounds, and typically also volatile compounds. They are less suitable for new engines and thus also environmentally more detrimental than newer sulfur and aromatic free base oils.

Nowadays, the use of recycled oils and renewable raw materials in the production of lubricants is frequently an object of interest. The use of renewable raw materials of biological origin instead of non-renewable fossil raw materials to produce hydrocarbon components is desirable, because the fossil raw materials are exhaustible and their effect on environment is detrimental. Problems associated with recycled oils include complicated purification and reprocessing steps to obtain base oils with high quality. Further, the development of a functioning and extensive recycling logistic system is expensive.

For the time being, only esters are used in lubricants of renewable and biological origin. The use of said esters is limited to a few special applications such as oils for refrigeration compressor lubricants, bio-hydraulic oils and metal working oils. In normal automotive and industrial lubricants, they are used mainly in additive scale. High price also limits the use of esters. In addition, the esters used in engine oil formulations are not interchangeable with other esters without performing new engine tests, even in cases where the chemical composition of the substituting ester is in principle similar. Instead, base oils consisting of pure hydrocarbon structure are partly interchangeable with each other. There are also some technical problems associated with esters. As polar compounds, esters suffer greater seal-swelling tendency than pure hydrocarbons. This has created lot of problems relating to elastomer in hydraulic applications. In addition, ester base oils are hydrolyzed more easily producing acids, which in turn cause corrosion on lubricating systems. Further, even greater disadvantage of esters is that additives developed for non-polar hydrocarbon base oils are not effective for ester base oils.

Ketones are commonly used as antifoam agents, mould release agents, and in mixtures with paraffin as metal coatings, as well as components of printing inks. Processes for producing ketones are known in the art, where the functional groups of the feed molecules react with each other forming a ketone. The carbon number of the ketone formed is reduced by one compared to the sum of the carbon numbers of the reacted feed molecules. Metals or oxides of alkaline earth metals are used as catalysts. EP 591297 describes a method for producing a ketone from fatty acids by pyrolysis reaction using a magnesium oxide catalyst. EP 0457665 discloses a method for producing ketones from triglycerides, fatty acids, fatty acid esters, fatty acid salts, and fatty acid anhydrides using a bauxite catalyst containing iron oxide.

Ketones may be reduced to paraffins using Wolff-Kishner reduction. The reaction involves converting a ketone to the corresponding hydrazone ($H_2NNH_2$) and decomposition of this intermediate in the presence of base at about 200° C. to yield the reduced alkyl derivative and nitrogen. Ketone is normally heated with hydrazine hydrate and sodium hydroxide at 100-200° C. temperature. Diethylene glycol or dimethyl sulfoxide is used as solvent. Alternatively, direct reduction of the carbonyl group to give a methylene group may be carried out with Clemmensen reduction reaction catalyzed by amalgam zinc and hydrochloric acid. Also a method for reducing ketones by catalytic hydrogenation with palladium on carbon catalyst at 50-150° C. temperature, under a hydrogen pressure between 0.1 and 0.5 MPa is known. With non-noble metals such as nickel, a higher temperature of nearly 200° C., and a hydrogen pressure of 30 MPa must be used as disclosed in *Ullmanns Encyclopädie der technischen Chemie*, 4. neubearbeitete und erweiterte Auflage, Band 13, Verlag Chemie GmbH, Weinheim 1983, Hydrierung p. 140.

FI 100248 presents a process with two steps wherein middle distillate is produced from plant oil by hydrogenation of the carboxylic acids or triglycerides of said plant oil to yield linear normal paraffins, followed by isomerization of said n-paraffins to give branched paraffins. The hydrogenation was performed at a temperature ranging from 330 to 450° C., under a pressure of higher than 3 MPa and liquid hourly space velocity (LHSV) being from 0.5 to 5 l/h. The isomerization step was carried out at 200 to 500° C. temperature, under elevated pressure, and LHSV being from 0.1 to 10 l/h.

EP 774451 discloses a process for isomerization of fatty acids or fatty acid alkyl esters. The isomerization of unsaturated fatty acids or fatty acid alkyl esters is performed using clay or another cationic catalyst. In addition to the main product, also feedstock dimers are obtained. After distillation, unsaturated branched fatty acids or fatty acid alkyl esters are obtained as the product.

GB 1 524 781 discloses a process for producing hydrocarbons from plant oil. In this process, the plant oil feed is pyrolyzed in three zones in the presence of a catalyst at temperature of 300-700° C. In the process hydrocarbons of the gas, gasoline, and diesel classes are obtained. They are separated and purified.

Starting materials originating from biological sources contain high amounts of oxygen. In processing oxygen is converted to water, carbon monoxide, and carbon dioxide. In addition, starting materials of biological origin often contain nitrogen, sulfur and phosphorus known as catalyst poisons and inhibitors of noble metal catalysts. They cause decreased service life of the catalyst, and make frequent regeneration of the catalysts necessary. Noble metal catalysts are used in isomerization processes. They are very expensive and highly sensitive to catalyst poisons.

Typical basic structural unit of plant and fish oils and animal fats is a triglyceride. Triglyceride is an ester of glycerol with three fatty acid molecules having the structure below:

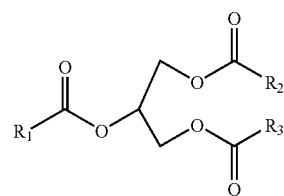

wherein $R_1$, $R_2$ and $R_3$ represent C4-C26 hydrocarbon chains. The length of the hydrocarbon chain is mainly 18 carbons (C18). C18 fatty acids are typically bonded to the middle hydroxyl group of glycerol. Typical carbon numbers of the fatty acids linked to the two other hydroxyl groups are even, being generally between carbon numbers C14 and C22.

Prior to processing, starting materials of biological origin are commonly pretreated with suitable known methods such as thermally, mechanically for instance by means of shear force, chemically for instance with acids or bases, or physically with radiation, distillation, cooling, or filtering. The purpose of chemical and physical pretreatments is to remove impurities interfering with the process or poisoning the catalysts, and reduce unwanted side reactions.

The pretreated biological raw material is often also preprocessed using a known method such as hydrolysis, transesterification, reduction, or saponification. Fatty acids may be produced from triglycerides by thermal pyrolysis treatment. In a hydrolysis reaction, oils and fats react with water yielding free fatty acids and glycerol as the product. Three main processes for the industrial production of fatty acids are known: Vapor splitting of triglycerides under high pressure, basic hydrolysis, and enzymatic hydrolysis. In the vapor splitting process, the hydrolysis of triglycerides using steam is carried out at temperatures between 100 and 300° C., under a pressure of 1-10 MPa, preferable conditions being from 250 to 260° C. and from 4 to 5.5 MPa. Metal oxides like zinc oxide may be added as the catalyst to accelerate the reaction. High temperature and pressure contribute to the dissolution of fats in water.

Fatty acid esters like triglycerides may be transesterified with an alcohol to obtain fatty acid alkyl esters. In the transesterification reaction the triglyceride structure is decomposed, the carboxylic acid yielding an ester with the alcohol, whereas the glycerol moiety of the triglyceride is liberated. Typically, methanol is used as the alcohol, but also other C1-C11 alcohols may be used. Sodium and potassium hydroxides dissolved in excess in methanol are used as catalysts. Typical conditions for the transesterification are as follows: Temperature between 60 and 70° C., pressure between 0.1 and 2 MPa. Esterification of free carboxylic acids with alcohol requires higher temperature and pressure (e.g. 240° C. and 9 MPa), or acidic conditions. For this reason, any free fatty acids present in the transesterification feed should be removed. Alternatively they can be separately esterified for instance using a sulfuric acid catalyst either before or after transesterification.

Acidic groups of fatty acids may be directly reduced to alcohols with lithium aluminium hydride, the double bonds thus remaining in alcohols, or in a manner used in industrial scale by hydrogenation of the fatty acid alkyl esters produced by transesterification to saturated alcohols. In the hydrogenation reaction, the alcohol moiety used for the transesterification is liberated and may be recycled. Fatty acid alkyl esters are reduced with metal catalysts, typically with copper chromite under a hydrogen pressure between 25 and 30 MPa, at 210° C. The C1-C3 alcohol liberated in the reaction is separated from the heavier fatty alcohol. Also chromium, iron or preferably rhodium activated nickel catalysts may be used at a temperature between 200 and 230° C. and under a hydrogen pressure of 25 MPa. Unsaturated alcohols are obtained in case a copper-zinc catalyst is used.

Fatty aldehydes may be produced from fatty alcohols by removing hydrogen in a dehydrogenation reaction. The reaction is opposite to the hydrogenation reaction of alcohols, and thus endothermic. In the dehydrogenation reaction corresponding hydrogenation catalysts are used but the temperature is higher, and thus side reactions such as cracking, isomerization, cyclization, and polymerization are possible. Supported copper chromite catalysts are typically used for producing aldehydes from alcohols. In gas phase dehydrogenation, typically a temperature between 250 and 400° C., and a pressure between 0.1 and 0.5 MPa are used. Moreover, it is generally known that corresponding aldehydes can be produced from alcohols using alumina, silica-alumina, hafnium oxide and zirconium oxide as catalyst. The products of the process are controlled by changes in process temperature. At low temperatures ethers are obtained, high temperatures give aldehydes, whereas olefins are typically obtained at 300-350° C.

Oils, fats and free fatty acids may be saponified in aqueous solutions by reaction with metal hydroxides such as alkali metal hydroxides yielding metal salts of fatty acids, and glycerol. In addition to sodium hydroxide, also for instance potassium oxide or zinc oxide may be used. In this case the formed soap has poor solubility in water and is readily isolated from the glycerol, which is soluble in water. In a traditional saponification process, the basic hydrolysis of triglycerides is performed at about 100° C., under normal pressure.

Neither the use of heteroatom containing starting materials of biological origin in a process for producing high-quality saturated base oils has not been disclosed, nor there are any reports about the use of heteroatom containing, optionally thermally and/or chemically and/or physically and/or mechanically treated intermediate materials of biological origin in a process for producing high-quality saturated base oils.

On the basis of the above teaching it may be seen that there is an obvious need for an alternative process for producing branched saturated hydrocarbon components from starting materials of biological origin. There is also a need for nonpolar saturated base oils complying with the quality requirements for high-quality base oils, said base oils being preferably of biological origin and having more preferable effects on the environment and for end users than traditional mineral base oils.

OBJECT OF THE INVENTION

An object of the invention is a process for producing a hydrocarbon component.

A further object of the invention is a process for producing a hydrocarbon component using starting materials of biological origin.

Another object of the invention is a process for producing a new type of base oil.

Still another object of the invention is a process for producing a diesel component.

Further, another object of the invention is a process for producing a gasoline component.

Another object of the invention is a process for producing saturated base oil and diesel component from starting materials of biological origin, said products mainly not containing heteroatoms.

An object of the invention is moreover a base oil complying with the requirements of the API Group III.

The characteristic features of the process and base oils of the invention are presented in the appended claims.

GENERAL DESCRIPTION OF THE INVENTION

Figure 1:
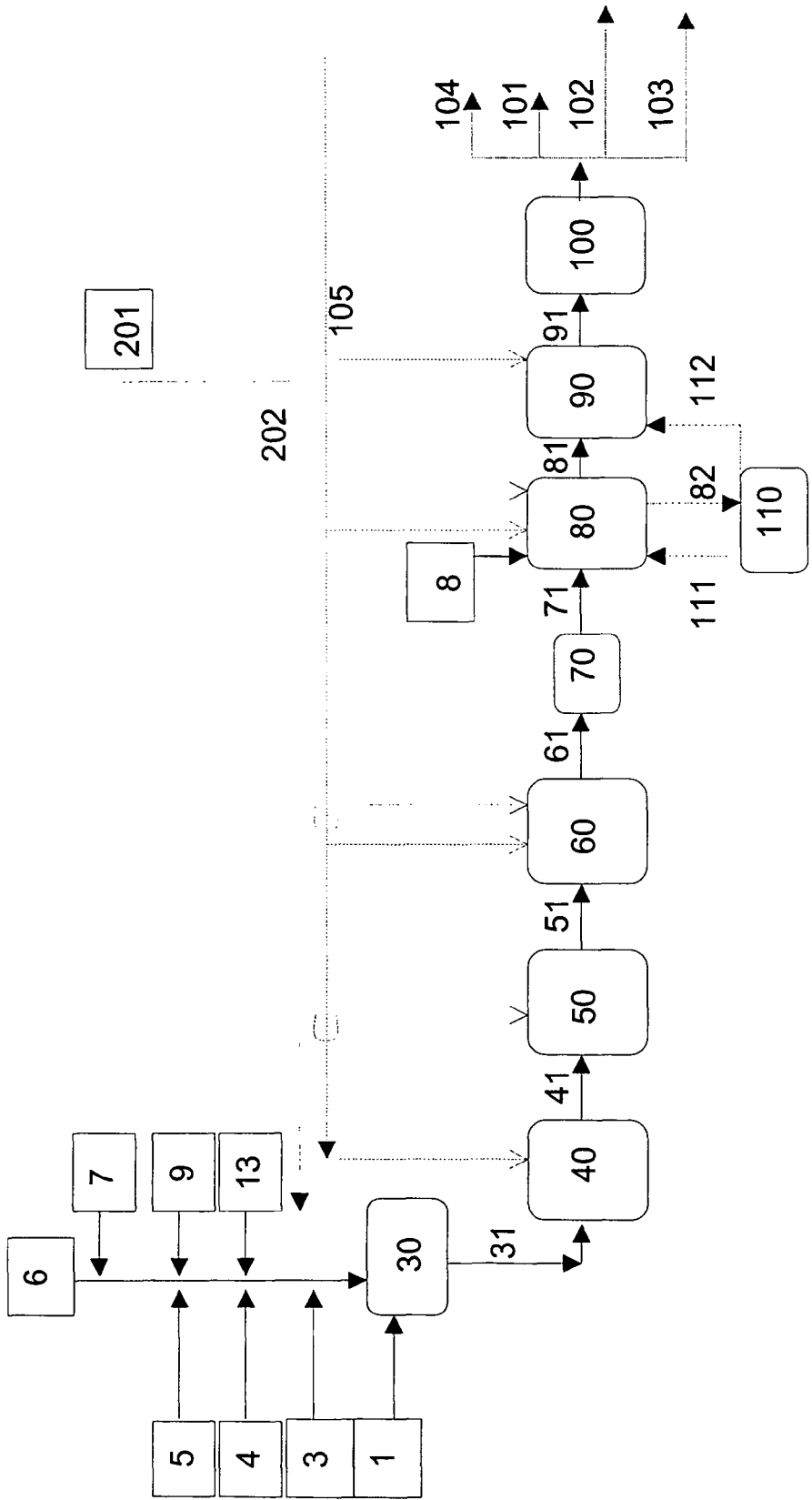
FIG. 1 is a schematic representation of a preferred embodiment of the invention for a process wherein the ketonisation is carried out prior to hydrodeoxygenation and isomerization.

The process of the invention for producing a hydrocarbon component, and particularly a high-quality saturated hydrocarbon base oil of biological origin, comprises a ketonisation step, a hydrodeoxygenation step and an isomerization step. The isomerization step refers here both to isomerization of unsaturated carboxylic acids and alkyl esters of carboxylic acids, particularly unsaturated fatty acids and fatty acid alkyl esters, and also isomerization of paraffins. Isomerization of fatty acids and fatty acid alkyl esters is performed prior to the ketonisation step, whereas the isomerization of paraffins is carried out following the ketonisation and HDO steps.

Carboxylic acids and their derivatives or combinations thereof, preferably fatty acids, fatty acid esters, fatty alcohols, fatty aldehydes, anhydrides of fatty acids, or metal salts of fatty acids of biological origin, are used as the feedstock of the process. Said starting materials of biological origin may be pretreated if necessary, and/or preprocessed using known methods.

Here, saturated base oil comprises saturated hydrocarbons. The term "saturated hydrocarbons" refers to paraffinic and naphthenic compounds, but not to aromatics. Paraffinic compounds may either be branched or linear. Naphthenic compounds are cyclic saturated hydrocarbons, or cycloparaffins, typically derived from cyclopentane or cyclohexane. A naphthenic compound may comprise a single ring structure (mononaphthene) or two isolated ring structures (isolated dinaphthene), or two fused ring structures (fused dinaphthene) or three or more fused ring structures (polycyclic naphthenes or polynaphthenes).

Here, ketonisation refers to the ketonisation reaction of carboxylic acids and the derivatives thereof, particularly fatty acids, corresponding esters, alcohols, aldehydes, anhydrides, and metal salts. In the reaction the functional groups of the feedstock react with each other yielding ketones. The ketonisation reaction of two carboxylic acids proceeds through an anhydride intermediate to give a ketone, water and carbon dioxide liberating in the reaction. In the pyrolytic ketonisation reaction of anhydrides and metal salts carbon dioxide is liberated. For alcohols and esters, the ketonisation reaction proceeds via aldehydes to give a Tishchenko ester and further to ketones, for aldehydes via Tishchenko esters to ketones. In these two last reactions carbon monoxide and hydrogen is liberated.

Fatty acids refer here to carboxylic acids of biological origin, having carbon numbers higher than C1.

Fatty acid esters refer here to triglycerides, fatty acid alkyl esters, esters of fatty acids with fatty alcohols, and natural waxes, all being of biological origin.

In this context, the term polyol refers to alcohols having two or more hydroxyl groups.

Here, hydrodeoxygenation (HDO) refers to oxygen removal from a compound by means of hydrogen. Water is liberated in the reaction, and simultaneously olefinic double bonds are hydrogenated and any sulfur and nitrogen compounds are removed. Reactions of the HDO step are exothermal. After the HDO step, the structure of the starting material has become paraffinic.

In this context, isomerization refers both to the isomerization of carboxylic acids and alkyl esters thereof, and to hydroisomerization.

Isomerization of unsaturated carboxylic acids or alkyl esters of carboxylic acids, particularly fatty acids or fatty acid alkyl esters refers here to their conversion to branched compounds without altering their carbon number.

Hydroisomerization refers here to the isomerization of linear paraffins to give branched paraffins.

In this context, carbon number range refers to the difference of the carbon numbers of the largest and the smallest molecules, plus one, in the final product. In this context, pressures are gauge pressures relative to normal atmospheric pressure.

Classification of the Periodic System of the Elements is the IUPAC classification.

Figure 2:
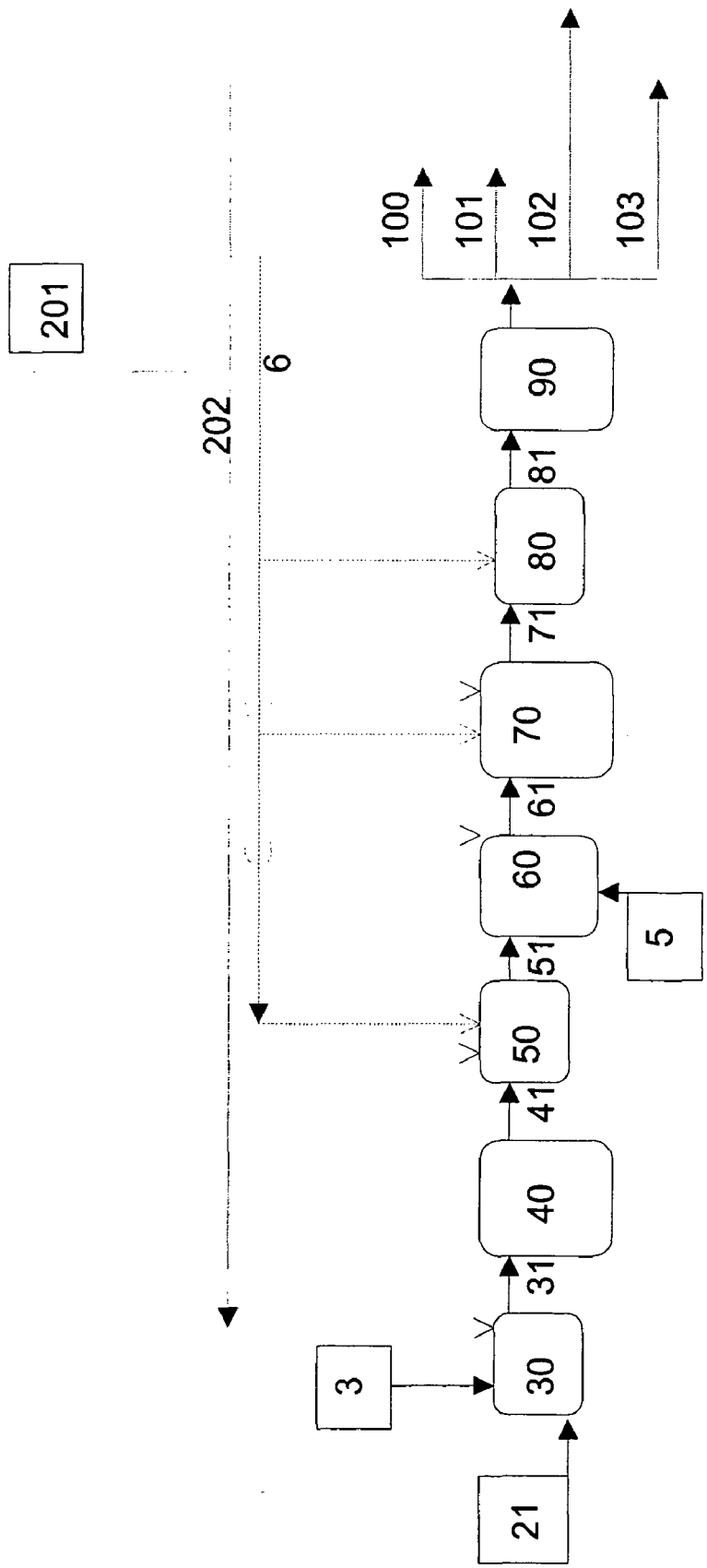
FIG. 2 is a schematic representation of a preferred embodiment of the invention for a process wherein fatty acids are isomerized prior to the ketonisation and hydrodeoxygenation steps.

The invention is now illustrated with the appended FIGS. 1 and 2 without wishing to limit the scope of the invention to the embodiments of said figures.

Figures

FIG. 1 shows schematically a preferable embodiment of the invention for a process wherein the ketonisation is carried out prior to hydrodeoxygenation and isomerization.

FIG. 2 shows schematically another preferable embodiment of the invention for a process wherein fatty acids are isomerized prior to the ketonisation and hydrodeoxygenation steps.

In FIG. 1, at least one of the following starting materials is introduced to the feed tank 30 either as separate components or as mixtures: fatty acids 4, fatty acid esters 9, aldehydes 5, alcohols 6 or acid anhydrides 7, and dicarboxylic acid feed 3 or polyols 13 is introduced as optional additional feedstock. Part of the lighter recirculated product fraction (for instance 102) or another hydrocarbon stream 201 may be optionally added to the feed tank 30 as a diluent. The diluent stream 202 comprises the recirculated stream 102 or hydrocarbon stream 201 or a mixture thereof. From the feed tank 30, the feedstock stream 31 and hydrogen stream 105 are passed to an optional prehydrogenation reactor 40, followed by the passing of the prehydrogenated stream 41 to the ketonisation reactor 50, optionally also receiving the diluent 202. From the ketonization reactor 50, the ketone product 51 and hydrogen stream 105 are passed to the hydrodeoxygenation reactor 60, optionally also receiving the diluent 202. The paraffinic product 61 from the hydrodeoxygenation reactor 60 is passed to stripping 70 where unwanted impurities are removed. Thereafter, the paraffinic product stream 71 and hydrogen stream 105 are passed to hydroisomerization reactor 80, optionally also receiving additional paraffinic feedstocks such as slack wax and Fisher-Tropsch waxes or waxes produced by gasification of biomaterial (biomaterial to liquids, BTL) 8, and the diluent 202. Following hydroisomerization 80, branched paraffins 81 may be subjected to optional hydrofinishing 90 using a hydrogen stream 105, followed by passing the product as the stream 91 to a distillation and separation unit 100. Branched paraffins 82 may optionally be passed from the hydroisomerization reactor 80 to dewaxing 110 wherein linear paraffins are removed either with solvents or catalytically in a known manner. Separated linear paraffins may be recirculated as stream 111 to the hydroisomerization reactor 80 for paraffins, while branched paraffins are passed as the stream 112 to the hydrofinishing reactor 90. In the distillation and/or separation unit 110, product components boiling at different temperature ranges and/or for special applications; gasses 104, gasoline 101, diesel 102, and base oil 103, are separated.

In FIG. 2, the unsaturated free fatty acid 3 and fatty acid alkyl ester feed 21 are introduced into the feed tank 30 as separate components or as mixtures. Part of the lighter product fraction to be recirculated (for instance 102) or another hydrocarbon 201 may be optionally passed to the feed tank 30 as a diluent. The diluent stream 202 comprises the recirculated stream 102 or hydrocarbon stream 201 or a mixture thereof. From the feed tank 30, the feedstock stream 31 containing fatty acids and/or fatty acid alkyl esters is passed to the isomerization reactor 40 for branching the components. Following isomerization, but prior to ketonisation, an optional prehydrogenation may be performed wherein branched fatty acid and/or fatty acids alkyl ester components are passed as the stream 41 to the double-bond prehydrogenation reactor 50 also receiving the hydrogen stream 6 and the optional diluent 202. Thereafter the fully saturated branched fatty acid and/or fatty acid alkyl ester feedstock 51 is introduced to the ketonization reactor 60 optionally also receiving the dicarboxylic acid feed 5, and the optional diluent 202. Following ketonization 60, the ketone product 61 and hydrogen stream 6 are passed to hydrodeoxygenation reactor 70 optionally also receiving the diluent 202. Following hydrodeoxygenation 70, the branched paraffinic product stream 71 and hydrogen stream 6 may be optionally passed to hydrofinishing 80. From the hydrofinishing reactor 80, the branched paraffinic product obtained is passed as the stream 81 to a distillation and separation unit 90 wherein product components boiling at different temperature ranges and/or for special applications; gas 100, diesel 102, and base oil 103, are separated.

DETAILED DESCRIPTION OF THE INVENTION

It was now surprisingly found that branched saturated hydrocarbon components, suitable as high-quality base oils, not containing heteroatoms may be obtained by the process of the invention. Feed selected from carboxylic acids and/or derivatives thereof, preferably fatty acids, esters of fatty acids, fatty alcohols, fatty aldehydes, anhydrides of fatty acids, and metal salts of fatty acids of biological or synthetic origin, or combinations thereof may be used in the process. In the process of the invention, ketonisation, hydrogenation, and isomerization reactions are utilized. Branched saturated hydrocarbon components are obtained as the product.

In the ketonisation reaction the length of the hydrocarbon chain of the feedstock is increased to such that only carbon-carbon bonds are left in the basic structure of the molecule. Such a ketone is not suitable as base oil. The oxygen present in the ketone group must be removed, and the low temperature properties must be improved for instance by making short branches to the molecular structure.

In the process of the invention, the feedstock is subjected to ketonisation, hydrodeoxygenation, and isomerization. In case unsaturated carboxylic acids and/or esters of unsaturated carboxylic acids, preferably fatty acids and/or fatty acid alkyl esters are used as the feedstock, the isomerization may be performed prior to ketonisation followed by hydrodeoxygenation, otherwise the isomerization is carried out after ketonization and hydrodeoxygenation steps.

Feed selected from the group consisting of carboxylic acids and derivatives thereof, preferably fatty acids, esters of fatty acids, fatty alcohols, fatty aldehydes, anhydrides of fatty acids, or metal salts of fatty acids, of biological origin, or combinations thereof is ketonised in the process. By this means the hydrocarbon chain length of the feedstock may be increased, and it preferably reaches the carbon number of the base oil. In the ketonisation step one may also utilize feedstocks that are different than those based on fatty acids. Such components are for example dicarboxylic acids or polyols. These feedstocks are ketonised at all the functional groups, thus increasing the molecular mass of the product compared to ketones formed of only two fatty acids. In this case, a polyketone molecule is formed, said polyketone being treated in a similar manner as monoketones. If necessary, the biological starting material may be subjected to one or more pretreatment or purification steps of the prior art for preparation of the feedstock before ketonisation reaction.

In the hydrodeoxygenation step of the process of the invention, the ketone is treated with hydrogen to give paraffins. The oxygen present in the ketone is liberated as water, and any other oxygen, nitrogen, and sulfur containing compounds are hydrogenated to paraffins, too. In addition, olefinic bonds are hydrogenated. After hydrodeoxygenation light hydrocarbons are removed as gases.

The hydrocarbon component obtained from the hydrodeoxygenation step may be subjected to hydroisomerization giving branched hydrocarbon chains. Following hydroisomerization step, the oxidation stability of the product may be improved using an optional finishing treatment. In addition, an optional dewaxing may be performed prior to or after the finishing.

In case unsaturated carboxylic acids or esters such as fatty acids and/or fatty acid alkyl esters are used as the feedstock, the isomerization may be carried out prior to ketonization, followed then by ketonization of the isomerized product, and the HDO step is performed as the last step of the process. In said isomerization, branches are formed in the structure of the compound, thus giving a mixture of isomerized components. Dimers, and to a lesser extent trimers of the feedstock components are obtained as by-products.

The steps of the process of the invention are preferably carried out in the order of ketonisation, hydrodeoxygenation, and as the last step isomerization.

The process may also be used for processing of mixtures feeds originating from biological starting materials and synthetic feedstocks, in which case additional synthetic feedstocks, or feedstocks produced with other processes may be used. Also pure synthetic feedstocks may be used, but then the products are not based on renewable natural resources. In the processing, in addition to paraffins of biological origin such as paraffins obtained in the process of invention or BTL paraffins produced in processes of biomaterial gasification, also Fischer-Tropsch waxes and/or Slack waxes obtained from crude oil by solvent dewaxing may be used as additional feedstocks in hydroisomerization. Of synthetic processes, the oxo-process and Fischer-Tropsch synthesis are stages in known processes for producing liquid products from starting materials containing carbon and hydrogen, such as from coal or natural gas.

Feedstock

The feed comprises at least one component selected from triglycerides, carboxylic acids having a carbon number C1-C38, esters of C1-C38 carboxylic acids with C-C11 alcohols, C1-C38 alcohols, C1-C38 aldehydes, C1-C38 carboxylic acid anhydrides, and metal salts of C1-C38 carboxylic acids. Preferable feedstocks are C4-C24 fatty acids of biological origin, and/or the derivatives thereof, mentioned above, or combinations thereof. Preferable components of the feedstock are C4-C24 fatty acids, C4-C24 fatty acid alkyl esters such as methyl esters, and esters of fatty acids with C12-C38 alcohols having long chains, natural waxes, C4-C24 fatty alcohols reduced from fatty acids, C4-C24 aldehydes reduced from fatty acids, C4-C24 fatty acid anhydrides, and metal salts of C4-C24 fatty acids. Dicarboxylic acids, polyols, triglycerides, and their mixtures with the above mentioned feedstocks may also be used as feed components.

Feed components are produced using any known methods, preferably from starting materials of biological origin, such as materials derived from plants, animals and fishes, selected from the group consisting of plant oils, plant waxes, plant fats, animal oils, animal fats, animal waxes, fish oils, fish fats, fish waxes. Corresponding starting materials derived from algae and insects are also contemplated as well as starting materials derived from aldehydes and ketones prepared from carbohydrates. C1-C38 and preferably C4-C24 fatty acids, or corresponding hydroxy acids or alcohols, act as structural units in suitable starting materials of biological origin. Since in the processing of fatty acids the service life of the catalyst is typically short, esters and alcohols may be optionally used as feedstocks causing less coke formation on the catalyst.

The starting materials of biological origin are suitably selected from the group consisting of:
a) plant fats, plant oils, plant waxes, animal fats, animal oils, animal waxes, fish fats, fish oils, fish waxes, and
b) free fatty acids or fatty acids obtained by hydrolysis, acid transesterification or pyrolysis reactions from plant fats, plant oils, plant waxes, animal fats, animal oils, animal waxes, fish fats, fish oils, fish waxes, and
c) esters obtained by transesterification from plant fats, plant oils, plant waxes, animal fats, animal oils, animal waxes, fish fats, fish oils, fish waxes, and
d) fatty acid alkyl esters obtained by esterification of alcohols with fatty acids of plant, animal and fish origin, and
e) fatty acid metal salts obtained by saponification of free fatty acids, plant fats, plant oils, plant waxes, animal fats, animal oils, animal waxes, fish fats, fish oils, fish waxes, and
f) alcohols and aldehydes obtained as reduction or hydrogenolysis products of free fatty acids, or fatty acids from plant fats, plant oils, plant waxes, animal fats, animal oils, animal waxes, fish fats, fish oils, fish waxes, and
g) fatty alcohols obtained by hydrolysis, transesterification and pyrolysis from waxes of biological origin, and
h) anhydrides of fatty acids from plant fats, plant oils, plant waxes, animal fats, animal oils, animal waxes, fish fats, fish oils, fish waxes, and
i) waste and recycled food grade fats and oils, and fats, oils and waxes obtained by genetic engineering, and
j) mixtures of said starting materials.

Metal salts are alkaline earth or alkali metal salts, preferably Ca, Zn, Mg, Al, or Na salts. Natural waxes are fatty acids esterified with alcohols having long hydrocarbon chains. The carbon number of fatty acid and alcohol hydrocarbon chains is typically from C12 to C38.

The starting material of biological origin may also be other than triglyceride, ester, fatty acid, alcohol or aldehyde, or a mixture of the said starting materials if the hydrocarbon chain length of the biological starting material is suitable or can be processed to be suitable to the level required for diesel and base oil applications.

If necessary, the starting material of biological origin may be pretreated or purified by suitable known methods as described above. For instance it may be distilled to fractions having narrower boiling ranges or carbon number distributions or ranges. Furthermore the impurities detrimental to the properties of the feedstock or final product may be removed by filtration through suitable filtering aids.

In addition to compound types described above, also totally or partly synthetic compounds, as well as mixtures of the compound types described above with synthetic compounds are also suitable feedstocks.

Examples of suitable biological starting materials include fish oils such as baltic herring oil, salmon oil, herring oil, tuna oil, anchovy oil, sardine oil, and mackerel oil; plant oils such as rapeseed oil, colza oil, canola oil, tall oil, sunflower seed oil, soybean oil, corn oil, hemp oil, olive oil, cottonseed oil, mustard oil, palm oil, peanut oil, castor oil, jatropha seed oil, palm kernel oil, and coconut oil; and moreover, suitable are also animal fats such as lard, tallow, and also waste and recycled food grade fats and oils, as well as fats, waxes and oils produced by genetic engineering. In addition to fats and oils, suitable starting materials of biological origin include animal waxes such as bee wax, Chinese wax (insect wax), shellac wax, and lanoline (wool wax), as well as plant waxes such as carnauba palm wax, ouricouri palm wax, jojoba seed oil, candelilla wax, esparto wax, Japan wax, and rice bran oil.

In the ketonization step of the process of the invention, also free carboxylic acids or esters thereof may optionally be used as feedstocks. These linear or branched mono and/or dicarboxylic acids may be produced by petrochemical processes or oxo processes. Suitable monocarboxylic acids include for instance propionic, butyric, isobutyric, 2-methyl butanoic, 2-ethyl butanoic, valeric, isovaleric, caproic, heptanoic, caprylic, pelargonic, isononanoic, caprinic, lauric, myristic, myristoleic, palmitic, palmitoleic, stearic, oleic, elaidic, linolic, linoleic, arachidonic, behenic, and lignin acids. Suitable dibarboxylic acids include for example the following: oxalic, malonic, succinic, glutaric, adipic, pimelic, suberic, azelaic, and sebasic acids.

In case where alcohols are ketonised in the process of the invention, also diols and/or polyols may be used as the feedstock in addition to fatty alcohols. Suitable diols include for instance diols derived from dicarboxylic acids, dimers of fatty alcohols, and 2,2-dimethyl-1,3-propanediol (NPG). Examples of suitable polyhydric alcohols include glycerol, 2-ethyl-2-hydroxymethyl-propane-1,3-diol (TMP), 2-methyl-2-hydroxyrnethyl-propane-1,3-diol (TME), 2-butyl-2-ethyl-propanediol (BEPD), and 2,2-bis-(hydroxymethyl)-1,3-propanediol (PET). Preferably alcohols containing tertiary carbons are not used when the thermal stability of the base oil to be produced has to be good.

Feedstocks used in the isomerization of unsaturated carboxylic acids, or alkyl esters of unsaturated carboxylic acids; particularly in the isomerization of unsaturated fatty acids or fatty acid esters, contain at least 20%, preferably at least 50%, and particularly preferably at least 80% by weight of compounds having double bonds. The feedstock may also be a mixture of unsaturated carboxylic acids and unsaturated carboxylic acid alkyl esters. Typically, the number of unsaturated bonds in compounds of the feedstock is 1 to 3. Preferably the feedstock comprises at least 40% by weight of monounsaturated fatty acids or fatty acid esters, more preferably at least 70% by weight. The feedstock may also comprise polyunsaturated fatty acids or fatty acid esters. The presence of an unsaturated bond in the molecule causes the formation of a cation as an intermediate, thereby facilitating the skeletal isomerization reaction.

Hydrocarbon may optionally be added as a diluent to the feedstock and/or in various process stages, such diluent may be for instance hydrocarbon of the middle distillate diesel class. Boiling ranges of hydrocarbons of the diesel class are between 150 and 400° C., typically between 180 and 360° C.

Process

In the process according to the invention, the feedstock is subjected to ketonisation, hydrodeoxygenation, and isomerization.

Isomerization Step of Unsaturated Carboxylic Acids and/or Esters

The isomerization may be carried out prior to the ketonisation step in case the feedstock comprises unsaturated carboxylic acids and/or alkyl esters of unsaturated carboxylic acids, preferably unsaturated fatty acids and/or unsaturated fatty acid alkyl esters. Acidic catalyst materials are used as the catalysts. Preferable the isomerization catalysts are aluminium phosphates, silica aluminium phosphates and zeolites, the catalyst preferably being a zeolite of the pentasil or mordenite type. The reaction temperature ranges from 150 to 350° C., preferably from 200 to 290° C., the reaction pressure being between 0 and 5 MPa, preferably between 0.1 and 2 MPa. Pressure is used to prevent lighter components from evaporating. Water or a lower alcohol may be added to the feedstock to suppress acid anhydride formation due to dehydration or dealcoholation. It is preferable to add water when the feedstock comprises unsaturated fatty acids and alcohol or when the feedstock comprises esters of unsaturated fatty acids. Typically the amount of added water or lower alcohol is 0-8%, and preferably 1-3% by weight based on the total reaction mixture. The lower alcohol is C1-C5 alcohol, and preferable alcohols are methanol, ethanol and propanol, with a greater preference given to those having the same alkyl group as that of the starting fatty acid ester to be isomerized. Excess water (more than 10%) should be avoided in order to prevent estolide formation. This skeletal isomerization step may also be carried out in the absence of water or lower alcohol. In case the reaction is performed as a batch reaction, the amount of the catalyst ranges from 0.01 to 30% by weight of the total reaction mixture, preferably from 0.5 to 10%, by weight. In the batch reactor, the reaction time is less than 16 hours, preferably less than 8 hours, particularly preferably less than 4 hours. In case a fixed bed reactor is used, the feed weight hourly space velocity (WHSV) is 0.1-100 l/h, where the amount of the feedstock is expressed in grams per hour per grams of the catalyst.

Prehydrogenation Step

The isomerized product obtained above, or the non-isomerized feedstock may be subjected to an optional prehydrogenation prior to the ketonisation step to reduce side reactions caused by the double bonds. Prehydrogenation is performed as a separate process under mild conditions. Prehydrogenation is performed in the presence of a prehydrogenation catalyst, at a temperature between 50 and 400° C., under a hydrogen pressure ranging from 0.1 to 20 MPa, the feed flow rate WHSV being between 0.1 and 10 l/h, the conditions preferably comprising temperatures between 100 and 300° C., hydrogen pressures ranging from 1 to 15 MPa, WHSV being from 0.5 to 5 l/h, particularly preferable conditions comprising temperatures between 150 and 280° C., pressures ranging from 2 to 10 MPa, WHSV being from 1 to 3 l/h. The prehydrogenation catalyst may contain metals of the Group VIII and/or VIA of the periodic system of the elements. The prehydrogenation catalyst is preferably a supported Pd, Pt, Ni, Ru, Rh, NiMo or CoMo catalyst, the support being activated carbon, alumina and/or silica.

The optionally prehydrogenated product from the isomerization of fatty acids and/or fatty acid alkyl ester, or the optionally prehydrogenated feedstock is passed to the ketonisation step yielding as the product a ketone with an increased hydrocarbon chain length. The obtained ketone is hydrogenated in the HDO step to give saturated hydrocarbons.

Ketonisation Step

In the ketonisation step, the pressure ranges from 0 to 10 MPa, preferably from 0.1 to 5 MPa, particularly preferably from 0.1 to 1 MPa, whereas the temperature ranges between 100 and 500° C., preferably between 100 and 400° C., particularly preferably between 300 and 400° C., the feed flow rate WHSV being from 0.1 to 10 l/h, preferably from 0.3 to 5 l/h, particularly preferably from 0.3 to 3 l/h. In the ketonisation step metal oxide catalysts may be used. Typical metals include Na, Mg, K, Ca, Sc, Cr, Mn, Fe, Co, Ni, Cu, Zn, Sr, Y, Zr, Mo, Rh, Cd, Sn, La, Pb, Bi, and rare earth metals. These metal oxides may be on a support, typical supports being laterite, bauxite, titanium dioxide, silica and/or aluminium oxide. The metal is preferably molybdenum, manganese, magnesium, iron and/or cadmium, the support being silica and/or alumina. Particularly preferably the metal is molybdenum, manganese and/or magnesium as oxide in a catalyst without support. No special catalysts are needed for the ketonisation of metal salts of fatty acids (soaps), since the metal present in the soap promotes the ketonization reaction.

Hydrodeoxygenation

In the HDO step of the invention, the ketone and hydrogen gas are reacted under a pressure ranging between 0.1 and 20 MPa, preferably between 1 and 15 MPa, particularly preferably from 2 to 10 MPa, the temperature being from 100 to 500° C., preferably from 150 to 400° C., particularly preferably from 200 to 350° C., the flow rate WHSV varying from 0.1 to 10 l/h, preferably from WHSV 1 to 5 l/h, and particularly preferably from WHSV 1 to 3 l/h. In the HDO step, special catalysts containing a metal of the Group VIII and/or VIA of the periodic system of the elements, on a support may be used. The HDO catalyst is preferably a supported Pd, Pt, Ni, NiMo or CoMo catalyst, the support being activated carbon, alumina and/or silica.

In a preferable embodiment, the reaction product obtained after the HDO step is purified for instance by stripping with steam, or with a suitable gas such as a light hydrocarbons, nitrogen or hydrogen. It is preferable for the process to remove impurities and water as efficiently as possible prior to the hydro isomerization step and/or finishing step.

In case the feedstock is already subjected to the isomerization of fatty acids and/or fatty acid alkyl esters, only optional finishing and separation steps are performed after the HDO and the optional purification steps.

Isomerization Step as Hydroisomerization

In case the isomerization of carboxylic acids and/or carboxylic acid alkyl esters was not carried out, a hydroisomerization step is carried out after the ketonisation, HDO and optional purification steps. In this case the hydrogenated product obtained from ketonisation followed by hydrodeoxygenation, and optional paraffinic additional feed are passed to the hydroisomerization reactor to react with hydrogen gas in the presence of a isomerization catalyst. In the hydroisomerization step, the pressure ranges from 0 to 20 MPa, preferably from 1 to 15 MPa, and particularly preferably from 4 to 10 MPa. The temperature ranges between 100 and 500° C., preferably between 200 and 400° C., and particularly preferably 250 and 370° C. The flow rate WHSV in between 0.1 and 10 l/h, preferably between 1 to 5 l/h, and particularly preferably between 1 and 3 l/h. In the hydroisomerization step, special isomerization catalysts containing molecular sieves and metals of the Group VIII of the periodic system of the elements, for instance Ni, Pt, and Pd, may be used. Alumina and/or silica may be used as supports.

Dewaxing Step

Following ketonisation, HDO and hydroisomerization steps of the feedstock, an optional dewaxing may be performed either catalytically or as solvent-based dewaxing. An optional dewaxing may also be carried out after the isomerization, ketonisation and HDO steps of unsaturated fatty acid and/or fatty acid alkyl ester feedstock.

In the catalytic dewaxing, hydrogen gas and the hydrogenated component, as well as the optional paraffinic additional feed react in the presence of a dewaxing catalyst. Zeolite catalysts comprising metals of the Group VIII of the periodic system of the elements such as Ni, Pt or Pd are used as dewaxing catalysts. In the dewaxing step, the pressure varies from 0.1 to 20 MPa, the temperature being between 100 and 500° C.

In the solvent-based dewaxing, linear paraffinic waxes are separated by dissolving the oil (hydrocarbon product) in a mixture of solvents, for instance methylethyl ketone and toluene. In the process, the solvent and the feed are passed in counter current manner and thus mixed. The mixture of oil and solvent is introduced to a cooling unit. Cooling results in the crystallization of the linear paraffinic waxes, whereas branched paraffins remain as oily liquids. The temperature used depends on the target low temperature properties of the product, the pour point of the final product decreasing as the temperature in dewaxing is decreased. Wax crystals are filtered from the mixture, collected for further processing, and the solvent is separated by evaporation from the base oil. Solvent-based dewaxing is also suitable for fatty acids and/or fatty acid alkyl esters after isomerization and prehydrogenation of the double bonds. Linear fatty acids and/or linear fatty acid alkyl esters are thus separated from the mixture of branched and non-crystallizable compounds by dissolving the feed for instance in hexane, and cooling as described above.

Finishing Step

The above obtained and optionally dewaxed product may optionally be finished for removing any double bonds and aromatics. In hydrofinishing, the finishing is performed using hydrogen in the presence of a catalyst, the pressure ranging from 1 to 20 MPa, preferably from 2 to 15 MPa, and particularly preferably from 3 to 10 MPa, and the temperature ranges between 50 and 500° C., preferably between 200 and 400° C., and particularly preferably between 200 and 300° C. In the hydrofinishing, special catalysts containing metals of the Group VIII of the periodic system of the elements, and a support may be used. The hydrofinishing catalyst is preferably a supported Pd, Pt, or Ni catalyst, the support being alumina and/or silica. Finishing may also be achieved by removing polar components using adsorption materials, such as clay or molecular sieves.

Following optional finishing, the product is passed to a distillation and/or separation unit in which product components boiling over different temperature range and/or product components intended for different applications are separated from each other.

If desired, the hydrocarbon component obtained as the product, or another suitable hydrocarbon may be used as a diluent in various stages of the process of the invention, such as in the ketonization, HDO and/or isomerization steps for increasing the conversion and/or selectivity and/or for controlling the exothermal nature of the reactions.

A fixed bed reactor, for instance the trickle bed reactor of the prior art is preferably used in prehydrogenation, HDO, hydroisomerization, and hydrofinishing steps.

Product

The process according to the invention yields a high quality branched and paraffinic hydrocarbon component suitable as a base oil or base oil component. The base oil product has excellent viscosity and low temperature properties. The process according to the invention also yields typically as a by-product a branched and paraffinic hydrocarbon product suitable for diesel fuel pool. The diesel component contains typically some short carbon-carbon side branches, resulting in an exceptionally low cloud point and cold filter plugging point but still a good cetane number. In addition, a hydrocarbon component suitable to be used as a solvent, gasoline and/or a component of gasoline is obtained as a by-product. All products are preferably of biological origin.

A branched, saturated and paraffinic hydrocarbon component is the main product in the process according to the invention, particularly when the ketonisation and hydrodeoxygenation steps are carried out prior to isomerization. A branched, saturated and paraffinic hydrocarbon component containing high amounts of cycloparaffins is obtained when carboxylic (fatty) acids are isomerized prior to the ketonisation and hydrodeoxygenation steps.

Feedstocks, which are preferably derived from biological starting materials, have a substantial effect on the composition and distillation range of the product. For instance feedstocks consisting of fatty acids may be fractionated by distillation to give narrow fractions to be tailored for various applications. For feedstocks having hydrocarbon chains of C16, C18, C20 and C22, typical carbon numbers of products are respectively C31, C35, C39, and C43. Narrow product fractions are obtained since the distillation range of the product mainly depends on the length of the hydrocarbon chain of the feedstock. Base oils with narrow distillation ranges obtained according to the invention have extremely low volatilities when compared to corresponding products of the prior art.

Carbon number range of the base oil of the invention is extremely narrow, typically no more than 5 carbons wide. Most typical structures and carbon number ranges (C31-C35) of the base oils 1 and 2 produced by the process of the invention (4-6 cSt/100° C.) are presented in Table 2. Carbon number depends on the carbon number of the feedstock. Most typical carbon numbers are shown bold-faced.

TABLE 2

Carbon numbers and structures of the base oils of the invention

| Base oil | Carbon number % by FIMS | Structure |
|---|---|---|
| 1 | C31/C33/C35 acyclic component about 90% mononaphthenes about 10% | 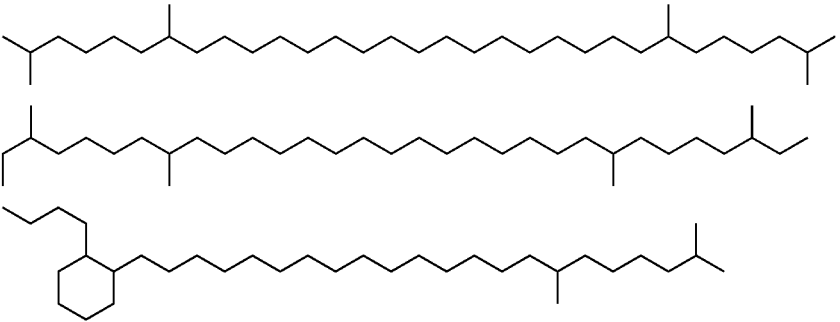 |

TABLE 2-continued

Carbon numbers and structures of the base oils of the invention

| Base oil | Carbon number % by FIMS | Structure |
|---|---|---|
| 2 | C31/C33/C35 acyclic component about 25% mononaphthenes about 50% dinaphthenes about 25% | 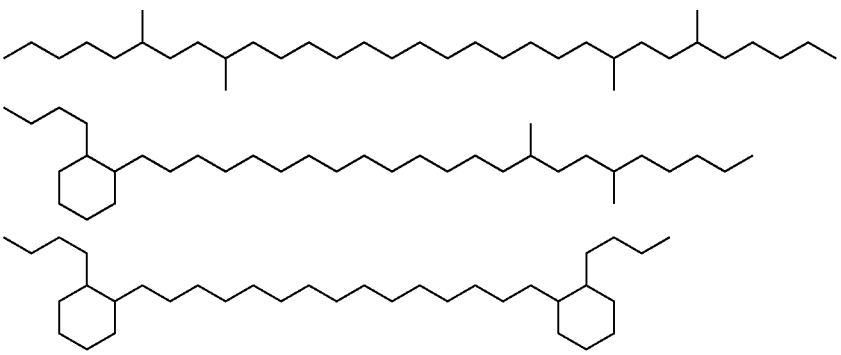 |

Base oils of biological origin shown in Table 2 are produced as follows:
1. Stearic acid fraction is ketonised, hydrodeoxygenated, and hydroisomerized.
2. Unsaturated fatty acid is isomerized, ketonised, and hydrodeoxygenated.

Using feedstocks with different hydrocarbon chains, the molecular masses of the products may be increased to reach viscosity ranges required for different applications by means of the ketonisation reaction. With the process of the invention, lighter hydrocarbon products such as solvents, gasoline, and diesel fuels may be produced from feedstocks of shorter hydrocarbon chains.

Saturated hydrocarbons are classified according to the carbon and hydrogen atoms by field ionization mass spectrometry (FIMS) method as follows:

| 1 | C(n)•H(2n + 2) | paraffins |
| 2 | C(n)•H(2n) | mononaphthenes |
| 3 | C(n)•H(2n − 2) | dinaphthenes |
| 4 | C(n)•H(2n − 4) | trinaphthenes |
| 5 | C(n)•H(2n − 6) | tetranaphthenes |
| 6 | C(n)•H(2n − 8) | pentanaphthenes |

In Tables 2 and 3, the percentages (%, by FIMS) refer to the groups of compounds determined according to said method.

In Table 3 are presented typical carbon number ranges (C25-C35) and compositions of synthetic (GTL) and mineral oil (VHVI and Slack Wax) base oils, belonging to the same viscosity class of about 4-6 cSt measured at 100° C. Structures of naphthenes are examples of different compound types. The average carbon numbers are shown bold-faced.

Products shown in Table 3 are produced as follows:
1. GTL is a hydroisomerized Fischer-Tropsch waxy fraction derived from natural gas
2. Slack Wax is a hydroisomerized Slack Wax fraction derived from crude oil
3. VHVI is a hydrocracked and hydroisomerized base oil derived from crude oil

TABLE 3

Carbon numbers and expected typical structures of synthetic base oils and base oils derived from crude oil

| Base oil | Carbon number %, by FIMS | Structure |
|---|---|---|
| 1 GTL | C25-C35, C29 acyclic component about 90% mononaphthenes about 10% | 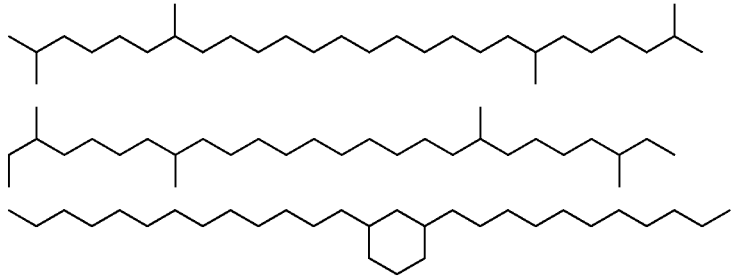 |

TABLE 3-continued

Carbon numbers and expected typical structures of synthetic base oils and base oils derived from crude oil

| Base oil | Carbon number %, by FIMS | Structure |
|---|---|---|
| 2 SLACK WAX | C25-C35, C28 paraffinic component about 70% mononaphthenes about 25% fused dinaphthenes about 5% | 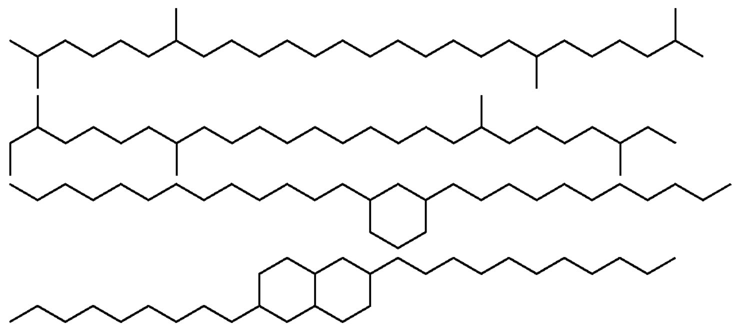 |
| 3 VHVI | C25-C35, C29 paraffinic component about 40% mononaphthenes about 35% fused dinaphthenes about 15% fused trinaphthenes about 5% fused tetralpentanaphthenes about 2-5% | 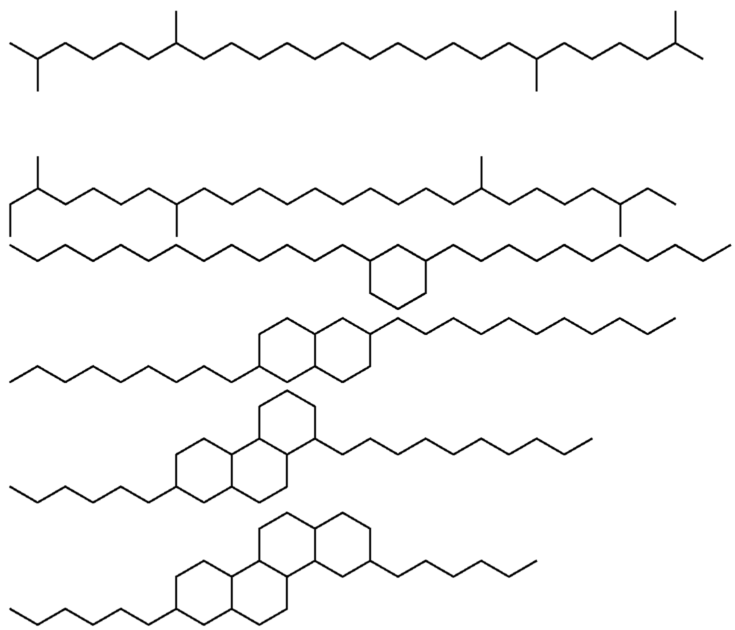 |

With respect to carbon number and molecular structure, base oils of the invention differ from products of the prior art, as may be clearly seen from Tables 2 and 3. In case the isomerization is based on the double bonds of C18 fatty acid skeleton (structure 2 in Table 1), the structure of the branched, saturated hydrocarbon product obtained using the process according to the invention is different from the one obtained for example when hydroisomerizing C25-C35 paraffins in Slack and GTL waxes. In the present case the branches are mainly in the middle of the long hydrocarbon chain, due to the common ω9 olefinic unsaturation positions responsible of branching. In Slack and GTL waxes (structures 1 and 2 in Table 3), the branches are mainly near the ends of the hydrocarbon main chain. There are typically alkyl branches having carbon numbers 1-4 within the hydrocarbon chain of the product. With respect to the branching site, the branched components are mixtures of different isomers. Branches more in the middle of the hydrocarbon chain lower the pour point considerably more than those at the ends of the chain.

In addition to the location of the branches, also the number of branches affects the pour point. The pour point being lowered by increasing number of branches, but at the same time also the viscosity index is reduced. It is known that an optimum correlation between the viscosity index and pour point is attained with only few branches present in the main hydrocarbon chain. In the process of the invention where the isomerization is based on the double bonds of C18 fatty acid skeleton, the number of branches is limited by the number of double bonds in the feedstock, and thus the base oil may not be branched too much to cause the VI to be reduced near the lower limit. In a similar manner, lowering of the pour point is limited by the number of double bonds in the feedstock.

In case the isomerization is based on hydroisomerization, such as of the C31/C33/C35 wax of hydrodeoxygenated ketone (structure 1 in Table 1), the structure of the branched, saturated hydrocarbon product obtained using the process according to the invention resembles to the one obtained hydroisomerizing C25-C35 paraffins in SW and GTL wax. In both present cases of the invention, the length of the hydrocarbon chain is though higher, typically from C31 to C35 and narrower than those of technically known base oils. Due to relatively long hydrocarbon main chain and controlled level of branching, the viscosity and cold properties of the product of invention are very good: the kinematic viscosity (KV100) is about 5 cSt and VI above 150 even though pour point is decreased to near −20° C.

Naphthenes of the final product of the invention are mononaphthenes and non-fused dinaphthenes. In the Slack wax and VHVI products of the prior art, the dinaphthenes are mainly fused. The VI of fused naphthenes is poorer than that of non-fused naphthenes. In addition, it is known that the non-fused naphthene rings are desirable as components of base oils since their VI is reasonably high but the pour point low. In the VHVI products of the prior art (structure 3 in Table 3), in addition to mononaphthenes there are polycyclic naphthenes with 3-5 rings typically not present in the product of the invention. These are formed as a result of cracking and hydrogenation of naphthenes and aromatic compounds of the mineral crude oil based feed.

In addition to pour point and viscosity index, the relationship of isoparaffins and 1-2 ring naphthenes to 3-6 ring naphthenes seem to play the major role in cold cranking. If too high amount of multiring naphthenes are present, they give higher CCS-30 values since they are present as an extremely viscous liquid. Furthermore, if normal paraffins are present after hydroisomerization, they give high CCS-30 values by crystallization and thus inhibiting the liquid to flow.

The base oil of biological origin according to the invention comprises a product produced from starting materials of biological origin. The base oil comprises branched hydrocarbons having carbon number at least C18. Said product contains not more than 20%, preferably not more than 10%, and particularly preferably not more than 5%, by weight, and at best not more than 1% by weight of linear paraffins, and at least 90%, preferably at least 95%, and particularly preferably at least 97%, by weight, and at best 99% by weight of saturated hydrocarbons.

Base oils of the invention comprise mono and dinaphthenes, but no polycyclic naphthenes, the dinaphthenes thereof being non-fused. Based on the FIMS analysis, the product of the invention contains mononaphthenes more than 5%, preferably 5-20%, particularly preferably 5-15%, and at best 5-10%; and less than 1.0%, preferably less than 0.5%, and particularly preferably less than 0.1% of polycyclic naphthenes measured by FIMS.

For base oils of the invention, having kinematic viscosity KV100 of 4-7 mm$^2$/s, the viscosity index is at least 115 and preferably at least 120, particularly preferably at least 150, and at best at least 160 (ASTM D 2270) and pour point lower than −9° C., preferably lower than −12° C. and particularly preferably lower than −15° C. (ASTM D 97/5950).

Low temperature dynamic viscosity, CCS-30, for base oil is no more than 29.797*(KV100)$^{2.7848}$ cP, preferably no more than 34.066*(KV100)$^{2.3967}$ cP; CCS-35 is no more than 36.108*(KV100)$^{3.069}$ cP, preferably no more than 50.501*(KV100)$^{2.4918}$ cP measured by method ASTM D 5293; pour point being not over −9° C., preferably not over −12° C. and particularly preferably not over −15° C. (ASTM D 97/5950).

For base oil of the invention the volatility of product, having KV100 from 3 cSt to 8 cSt, is no more than 2271.2*(KV100)$^{-3.5373}$% by weight as determined by the method of DIN 51581-2 (Mathematical Noack method based on ASTM D 2887 GC distillation).

Width of the carbon number range of base oils of the invention is no more than 9 carbons, preferably no more than 7 carbons, particularly preferably no more than 5 carbons, and at best 3 carbons (FIMS). More than about 50%, preferably more than 75% and particularly preferably more than 90% by weight of the base oil contain hydrocarbons belonging to this narrow carbon number range.

Distillation range of base oils of the invention is no more than 155° C., preferably no more than 100° C., particularly preferably no more than 70° C., and at best no more than 50° C. (determined by the method of ASTM D 2887, distillation points D10 and D90).

Sulfur content of said base oil of the invention is less than 300 ppm, preferably less than 50 ppm, and particularly preferably less than 1 ppm, (ASTM D 3120).

Nitrogen content of said base oil of the invention is less than 100 ppm, preferably less than 10 ppm, and particularly preferably less than 1 ppm, (ASTM D 4629).

Base oils of the invention, based on biological starting materials, contain carbon $^{14}$C isotope, which may be considered as an indication of the use of renewable raw materials. Typical $^{14}$C isotope content (proportion) of the total carbon content in the product, which is completely of biological origin, is at least 100%. Carbon $^{14}$C isotope content is determined on the basis of radioactive carbon (carbon $^{14}$C isotope) content in the atmosphere in 1950 (ASTM D 6866). $^{14}$C isotope content of the base oil according to the invention is lower in cases where other components besides biological components are used in the processing of the product, said proportion being, however, more than 50%, preferably more than 90%, particularly preferably more than 99%. In this way, even low amounts of base oil of biological origin may be detected in other types of hydrocarbon base oils.

The cetane number of the diesel product obtained with the process of the invention, is more than 40, preferably more than 55, and particularly preferably more than 70. It contains more than 60%, preferably more than 99% by volume, of paraffins, and less than 30%, preferably less than 1% by volume, of aromatics, based on the IP-391 method. The product comprises less than 40%, preferably less than 10%, by weight, of linear n-paraffins. The cloud point of the diesel component is less than 0° C., preferably less than −15° C., and particularly less than −30° C. Typically, the diesel product obtained is totally of biological origin. In the product of the invention, there are branches formed by carbon-carbon bonds, this structure resulting in a very low cloud point.

ADVANTAGES OF THE INVENTION

The process of the invention allows particularly for the use of renewable starting materials of biological origin, containing heteroatoms, for producing base oils, but also diesel and gasoline components. In addition to traditional crude oil, a completely new raw material source for high-quality branched paraffinic base oils is provided according to the invention. Also carbon dioxide emissions contributing to the greenhouse effect may be reduced by using renewable raw material sources instead of non-renewable ones.

According to the process of the invention, base oil containing only carbon and hydrogen is obtained, the stability of said base oil in humid conditions being higher than that of esters or other base oils containing heteroatoms. A paraffinic hydrocarbon component is not decomposed as easily as esters that form corrosive acids. A nonpolar and fully saturated hydrocarbon component free of sulfur is obtained using the process of the invention by removing oxygen of ketones, and the heteroatoms of any impurities of the feedstock in the HDO step. In the isomerization step, the carbon chain is branched, thus improving low temperature properties, that is, the pour point is lowered, low-temperature fluidity enhanced and filterability at low temperatures is improved. Solid wax is converted to oily hydrocarbon having viscosity index (viscositytemperature-dependence) very suitable for top-tier base oils without blending limitations, and further, it is compatible with lubricant additives.

With the process of the invention, high-quality saturated base oil having a low pour point may be produced, said base oil being also very useful at low temperature conditions. The product is typically free of sulfur, the viscosity index thereof being preferably at least 120, and thus it may also be suitably used in applications of Group III base oils.

Composition, properties and boiling range of the product are also strongly influenced by the starting material of biological origin. The starting material may be distilled to fractions according to carbon numbers. According to the invention, branched paraffinic base oil having narrow boiling ranges and different physical properties may be processed from these fractions. Typical carbon number ranges of the product components are as follows: gas C1-C4, gasoline C5-C10, diesel C11-C26, and base oil having carbon number of at least C18. Distillation range of base oil produced from a feedstock having a single carbon number is the narrowest.

Narrow distillation range indicates that the product does not contain initial light fraction, meaning molecules considerably lighter than the average, which can be seen as decreased volatility of the product, resulting in reduced emissions and reduced use of lubricants in practical applications. The "tail" composed of the heavier components, meaning molecules considerably heavier than the average, is also missing from the product. This results in excellent low temperature properties of the product.

For the base oil of the invention, the carbon number and distillation range are governed by the feedstock composition. For base oils of the prior art, the distillation range is adjusted by distilling the product to obtain a fraction having the desired kinematic viscosity. It is preferable that lubricants have base oils with narrow carbon number distribution and thus narrow distillation range, so that lubricating oils contain molecules of similar sizes behaving in a similar way under different conditions.

The base oil according to the invention has high viscosity index, which leads to a significantly decreased need of high price Viscosity Index Improver (VII) or in other terms Viscosity Modifier (VM). It is commonly known, that the VII is an additive, which causes highest amount of deposits in vehicle engines. In addition, reduction of the amounts of VII results in significant savings in costs.

Also, because the base oil is non-toxic, contains no sulfur, nitrogen or aromatic compounds typically present in the conventional mineral oil based products, it may more safely be used in applications where the end user is exposed to oil or oil spray.

Moreover, response of the base oil according to the invention is extremely high for antioxidants and pour point depressants, and thus the life time of the lubricating oils are longer and they can be used in the colder environment than lubricants based on the conventional base oils.

Even though the branched, saturated hydrocarbon product is produced from saturated and unsaturated natural fatty acids, it contains no oxygen, and thus its hydrolytic stability is much higher than that of synthetic ester base oils. Due to the lack of ester bonds, also the formation of acidic degradation products is minimized. In addition, the oxidation stability of the saturated base oil is higher than that of ester base oil containing unsaturated fatty acid structural units.

Compared to esters, the base oil of the invention is more compatible with conventional base oils derived from crude oil, base oils obtained from Fischer-Tropsch process, and with hydrocarbon base oils, as well with lubricant additives. Moreover, it is compatible with elastomers, and thus it can be used in modern vehicle engines without modifications.

An additional advantage of the base oil according to this invention is that it fulfils the API group III base oil specifications. Therefore it can be used in engine oil formulations like other group III base oils according the same interchanging rules without need to perform new engine tests.

The base oil of the invention is preferably based on renewable natural resources. Starting materials of the process of the invention are available all over the world, and moreover, the utilization of the process is not limited by significant initial investments in contrast for instance to the GTL technology.

The products of the inventive process are carbon dioxide neutral with respect to the use and disposal thereof, that is, they will not increase the carbon dioxide load of the atmosphere in contrast to products derived from fossil starting materials.

Further advantages of the invention relate to diesel fuel component of biological origin, which has excellent low temperature properties and cetane number compared to those of solutions of the prior art, where components based on fatty acid methyl esters are used. Problems associated with low temperature properties have been avoided by isomerizing waxy n-paraffins derived from fatty acids to give isoparaffins.

The middle distillate diesel fuel component obtained is a high-quality hydrocarbon component of biological origin particularly suitable as a component for diesel fuel, as isoparaffinic solvent, and as lamp oil, the cetane number thereof being even above 70, the cloud point being as low as below $-30°$ C. Fouling of the engine may be expected to be reduced in comparison to fuels of biological origin already known in the art, said fuels containing incompletely burning ester components. Moreover, the density of the composition is lower. The composition requires no changes of the automobile technology or logistics. Higher energy content of the biological component per unit volume compared to products based on esters may also be mentioned as an advantage.

With the optional prehydrogenation step side reactions of double bonds of hydrocarbon chains may be reduced. Side reactions, such as polymerization, ring formation and aromatization cause coke formation on the catalyst, thus reducing its service life. Ring formation and polymerization change also viscosity properties of the hydrocarbon components. Moreover, said prehydrogenation results in improved yields of the final base oil product.

In addition to hydrocarbon chain lengthening also oxygen may be removed from the feedstock as carbon dioxide with the ketonization reaction, which is favorable for the process to minimize hydrogen consumption. With the isomerization, low temperature properties of the product may be improved without interfering with viscosity properties.

With the solution of the invention, high hydrogen partial pressure may be maintained throughout the whole process, and keep levels of impurities low. Carbon monoxide, carbon dioxide and water contents may be lowered to such an extent that light stripping in the HDO stage or in a separate gas/liquid separation vessel is sufficient to remove residual impurities prior to isomerization.

Advantages of the invention also include protection of the isomerization catalyst, thus preventing the deactivation thereof.

The properties of the hydrocarbon components produced with the process according to the invention are excellent, and moreover, distillation ranges of products produced from fatty acids with a specific carbon number are considerably narrower that those of VHVI base oils. The products are well suited as base oils without blending limitations, and further, the products are also compatible with lubricant additives.

EXAMPLES

The invention is now illustrated by means of the following examples without wishing to limit the scope of the invention thereby. Properties of the hydrocarbon components prepared in the examples are presented in Table 4. Similarly, properties of some of the base oils of the prior art are shown in Table 5. It is however clear that the invention is not limited to embodiments described in the examples.

Example 1

Preparation of a Hydrocarbon Component from Stearic Acid Fraction ($C_{17}H_{35}COOH$)

A mixture of plant oils (linseed, soybean, and rapeseed oils) was pretreated by hydrolysis and distillation to obtain fatty acid fractions according to carbon numbers. The C18 acid fraction thus obtained was used as the feed, the fraction being diluted with a paraffinic diesel fuel of biological origin. C18 acid content of the feedstock thus obtained was 31%, by weight. Double bonds of the feedstock were selectively prehydrogenated, and the stearic acid was continuously ketonised at atmospheric pressure, in a tubular reactor using a $MnO_2$ catalyst. Temperature of the reactor was 370° C., the WHSV of total feed being 3 l/h. 22% by weight of 18-pentatriacontanone, or stearone, in a diluent was obtained as the ketonisation product.

In the next step, the stearone/diluent mixture obtained above was hydrodeoxygenated in a high pressure Parr reactor using a dried and activated $NiMo/Al_2O_3$ catalyst, to give linear paraffins. The ketone was hydrogenated at 330° C., under a pressure of 5 MPa, mixing at 300 rpm until no ketone peak was detected in the FTIR spectrum. 71% by weight of linear C35 paraffin was obtained from stearic acid.

The paraffin wax obtained above was isomerized in a Parr reactor to give a branched paraffin of the base oil class using a reduced Pt molecular sieve/$Al_2O_3$ catalyst. Preheated mixture of the paraffin/diluent was isomerized under a hydrogen pressure of 3 MPa and at 340° C. until a pour point of −6° C. was obtained. Finally, light fractions were distilled from the product at reduced pressure, followed by finishing of the paraffinic product by filtering through kieselguhr. Hydrocarbon components may be produced in a similar way from other fatty acids and dicarboxylic acids.

Example 2

Preparation of a Hydrocarbon Component from Fatty Acids Derived from Palm Oil Palm oil was hydrolyzed. Fatty acids derived from palm oil were used as the feedstock following selective prehydrogenation of the double bonds of said fatty acids. After hydrogenation, the fatty acid composition was as follows: C14 1%, C16 44%, C18 54%, and C20 1%, all percentages being by weight. The fatty acids were ketonised as in Example 1. Following ketonization, the solvent was distilled off, yielding a product with the following composition: C15SCOC15 ketone, 10.4%, C15COC17 ketone, 42.1%, and C17COC17 ketone, 43.6%, by weight.

The ketone mixture obtained from the ketonisation stage was hydrodeoxygenated in a Parr reactor using a dried and activated $NiMo/Al_2O_3$ catalyst to give linear paraffins. Hydrodeoxygenation was carried out under a pressure of 3.3 MPa, at 330° C., mixing at 300 rpm. Linear paraffin with the composition: C33 chain 41.8%, C34 chain 2.1%, and C35 chain 43.8% by weight was obtained from palm oil.

The linear paraffin wax obtained in the HDO step was isomerized in a Parr reactor to give branched paraffins of the base oil class using a reduced Pt molecular sieve/$Al_2O_3$ catalyst. Isomerization was performed at 340° C., under a hydrogen pressure of 3 MPa until the pour point of the product was below −15° C. Finally, light fractions were distilled off under reduced pressure.

Palm oil also contains C16 and C18 fatty acids, the hydrocarbon component thus having a wider distillation range and a lower kinematic viscosity compared to the product of Example 1. Hydrocarbon components may also be produced in a similar way from other plant and fish oils, and animal fats.

Example 3

Preparation of a Hydrocarbon Component from Methyl Esters of Fatty Acids Derived from Animal Fats Purified animal fat was transesterified under basic conditions with methanol at 70° C., under a pressure of 0.1 MPa, in the presence of a sodium methoxide catalyst in two steps, thus producing methyl esters of fatty acids. The reaction mixture was purified by washing with acid and water, and the mixture of fatty acid methyl esters was dried. The fatty acid composition of the mixture of methyl esters derived from animal fat was as follows: C14:0 2%; C16:0 23%, C16:1 3%, C18:0 13%, C18:1 40%, C18:2 11%, C18:3 1% by weight.

The mixture of fatty acid methyl esters obtained above was used as the feedstock of the process, diluted with paraffinic diesel of biological origin. The fatty acid methyl ester content of the feedstock was 30% by weight, the feedstock being continuously ketonised in a tubular reaction as described in Example 1. Both saturated and unsaturated ketones were obtained as the product. Their carbon numbers were as follows: 10% of C21-C28 ketones, 3% of C29 ketone, 10% of C31 ketone, 33% of C33 ketone, and 20% by weight of C35 ketone.

The ketone mixture was first hydrodeoxygenated a Parr reactor as described in Example 2, followed by isomerization according to Example 2. Hydrocarbon components may also be produced in a similar manner from methyl esters derived from plant and fish oils. Service life of the ketonization catalyst may be extended by using less corrosive methyl esters instead of fatty acids.

Example 4

Preparation of a Hydrocarbon Component from Metal Stearates

A metal stearate $(CH_3(CH_2)_{16}COO)_2Mg$ was ketonised under atmospheric pressure in a Parr reactor at 340° C. and with mixing rate of 300 rpm. Stearone, or C35 ketone, obtained as the product was hydrodeoxygenated and isomerized as described in Example 1. The product thus obtained correspond the product of Example 1. Hydrocarbon components may also be produced in a similar manner from other metal salts of fatty acids derived from plant oils, animal fats and fish oils, as well as from metal salts of fatty acids obtained by saponification of plant and fish oils or animal fats. No special catalyst is needed for the ketonization in case metal salts are used.

Example 5

Preparation of a Hydrocarbon Component from Carboxylic Acids of Tall Oil

Distilled tall oil fatty acids were isomerized in a Parr high-pressure reactor with mordenite type zeolite. Tall oil fatty acids, 5 wt-% of the catalyst and 3 wt-% of water, calculated of total reaction mixture, were placed in a reactor and air was removed from the autoclave with purging nitrogen. The mixture was stirred with 300 rpm. The reactor was heated to 280° C. and kept under nitrogen atmosphere of 1.8 MPa for 6 hours. After cooling, the reaction mixture obtained was taken from the autoclave, and the zeolite was filtered off. The filtrate was distilled under reduced pressure to yield monomeric acids.

The monomeric acids thus obtained were placed in an autoclave, and double bonds were hydrogenated at 150° C. with a catalyst containing 5 wt-% Pd on carbon under hydrogen atmosphere of 2 MPa until the reaction was complete. Catalyst amount was 2 wt-% of monomeric acid. Then, the reaction mixture was cooled, and the catalyst was filtered off.

The obtained crude branched chain fatty acids were subjected to a conventional solvent fractionation procedure to yield isomerized fatty acids. To the crude branched chain fatty acids, about 2-fold amount by weight of hexane was added. After this mixture was cooled to −15° C., the resulting crystals of non-isomerized fatty acids were filtered off. Then, the hexane was distilled off from the filtrate to yield purified isomerized fatty acids.

The isostearic acid was diluted with a paraffinic diesel of biological origin in a ratio of 30/70%, by weight. The mixture thus obtained was continuously ketonised at atmospheric pressure in a tubular reactor using a $MnO_2$ catalyst. The temperature of the reactor was 370° C., the WHSV being 1.7. A mixture of isomerized ketones was obtained as the product.

The mixture of isomerized ketones was hydrogenated in a HDO step in a Parr reactor as in Example 2. Solvents were distilled from the final product under reduced pressure. Thereafter, the product was subjected to solvent dewaxing to remove linear paraffins, and finally, the paraffinic product was finished by filtering through kieselguhr. Mainly branched paraffins were obtained as the final product. Hydrocarbon components may also be produced in a similar way from other isomerized fatty acids or from isomerized methyl esters of fatty acids of plant, animal and fish origin.

Example 6

Preparation of a Hydrocarbon Component from Tall Oil Fatty Acids and Dicarboxylic Acids Distilled mixture of fatty acids from tall oil was isomerized and prehydrogenated as described in Example 5. The isostearic acid fraction thus obtained and the C6 dicarboxylic acid (adipic acid) were mixed in a molar ratio of 1:3, and the mixture was ketonised under atmospheric pressure in a Parr reactor using a MgO catalyst at 340° C., with mixing rate of 300 rpm.

The ketone mixture was hydrogenated in the HDO step in a Parr reactor as in Example 1, and light fractions were separated by distillation from the final product under reduced pressure. In comparison to other Examples, branched paraffins having longer chains were obtained as products. Hydrocarbon components may also be produced in a similar manner from other fatty acids or fatty acid methyl esters of plant, animal and fish origin and dicarboxylic acids. Either the fatty acids, or alternatively the wax obtained after ketonisation and hydrodeoxygenation may be subjected to isomerization.

TABLE 4

Properties of the products produced in Examples 1-6

| | Analysis | | | | | |
|---|---|---|---|---|---|---|
| | Examp 1 | Examp 2 | Examp 3 | Examp 5 | Examp 6 | Method |
| KV100 (mm²/s) | 5.2 | 4.3 | 5.8 | 6.5 | 16.4 | ASTM D445 |
| KV40 (mm²/s) | 23.0 | 18.3 | 27.7 | 34.0 | 150.5 | ASTM D445 |
| VI, ( ) | 164 | 153 | 159 | 148 | 115 | ASTM D2270 |
| Pour point (° C.) | −6 | −21 | −18 | −12 | −12 | ASTM D5950 |
| GC-distillation (° C.) | | | | | | ASTM D2887 |
| 10% | 419 | 375 | | 455 | | |
| 50% | 475 | 457 | | 481 | | |
| 90% | 486 | 474 | | 497 | | |
| GC-Noack volatility, wt-% | 5.8 | 12.5 | | 4.2 | | DIN 51581-2 |
| Molecular distribution, wt-% | | | | | | |
| n-Paraffins | <1 | | | <1 | | GC |
| i-Paraffins | 88 | | | 31 | | FIMS |
| Mononaphthenes | 12 | | | 49 | | FIMS |
| Dinaphthenes | 0 | | | 20 | | FIMS |
| Other naphthenes | 0 | | | 0 | | FIMS |
| Sulfur, ppm | <1 | | | 1 | | ASTM D3120/D4294 |
| Nitrogen, ppm | <1 | | | <1 | | ASTM D4629 |

TABLE 5

Properties of the base oils of the prior art.

| | Analysis | | | | |
|---|---|---|---|---|---|
| | API GpIII, HC-CDW | API GpIII, HC-CDW | API GpIII, SW | API GpIV, PAO | Method |
| KV100 (cSt) | 4.29 | 6.00 | 4.0 | 5.7 | ASTM D445 |
| KV40 (cSt) | 20.0 | 33.1 | 16.8 | 30 | ASTM D445 |
| VI | 122 | 128 | 140 | 135 | ASTM D2270 |
| Pour point (° C.) | −18 | −12 | −21 | <−63 | ASTM D5950 |
| CCS at −30° C. (cP) | 1750 | 4100 | | 2300 | ASTM D5293 |
| CCS at −35° C. (cP) | 3100 | 7800 | 1560 | 3850 | ASTM D5293 |
| GC distillation (° C.) | | | | | ASTM D2887 |
| 10% | 395 | 412 | 394 | | |
| 50% | 421 | 459 | 421 | | |
| 90% | 456 | 513 | 459 | | |
| GC-Noack, w-% | 13.3 | 5.8 | 12.5 | | DIN 51581-2 |
| Molecular distribution, wt-% | | | | | |
| Aromatics | 0.0 | 0.0 | 0.0 | 0.0 | ASTM D2549 |
| Paraffins | 37.0 | 26.8 | 72.4 | 100 | FIMS |
| Mononaphthenes | 37.3 | 39.3 | 23.9 | 0 | FIMS |
| Dinaphthenes | 16.1 | 20.3 | 3.5 | 0 | FIMS |
| Other naphthenes | 9.8 | 13.6 | 0.2 | 0 | FIMS |
| Sulfur, ppm | <0.2 | <0.2 | | <1 | ASTM D3120/D 4294 |
| Nitrogen, ppm | <1 | <1 | | <1 | ASTM D4629 |

HC-CDW = hydrocracked, catalytically dewaxed base oil

Example 7

Preparation of a Hydrocarbon Component from Fatty Acids Derived from Palm Oil Palm oil was hydrolyzed. Fatty acids derived from palm oil were used as the feedstock following selective prehydrogenation of the double bonds of said fatty acids. The fatty acids were vaporized with nitrogen purge in a separate vaporizer unit and ketonised continuously at atmospheric pressure, in a tubular reactor using a $MnO_2$ as catalyst. Temperature of the reactor was 380° C., the WHSV of the feed being 1 l/h−1.

The C31, C33, C35 ketone mixture obtained from the ketonisation stage was hydrodeoxygenated continuously in a tubular fixed bed reactor using a dried and activated NiMo/$Al_2O_3$ catalyst to give linear paraffins. Hydrodeoxygenation was carried out under a pressure of 4 MPa (40 bar), at 270° C. and with WHSV of 1 l/h.

The linear paraffin wax obtained in the HDO step was isomerized continuously in a tubular fixed bed reactor using a reduced Pt molecular sieve/$Al_2O_3$ catalyst to give branched paraffins using a reduced Pt molecular sieve/$Al_2O_3$ catalyst. Isomerization was performed at 340° C., under a hydrogen pressure of 4 MPa until the pour point of the product was below −15° C. Finally, light fractions were distilled under reduced pressure and separated.

Hydrocarbon components may also be produced in a similar way from other plant and fish oils, and animal fats.

TABLE 6

Properties of the products in example 7.

| Method | Analysis | baseoil >413° C. | baseoil 356-413° C. | diesel 170-356° C. |
|---|---|---|---|---|
| ASTM D 4052 | Density@15° C., kg/m3 | 821.8 | 810.1 | 775.3 |
| ASTM D 5950 | Pour Point, ° C. | −23 | −32 | |
| ASTM D 5771 | Cloud Point, ° C. | −6.8 | −24.7 | <−50 |
| EN 116 | Cold Filter Plug Point, ° C. | | | <−45 |
| ENISO 2719 | Flash point PMcc, ° C. | | | 84.0 |
| | IQT cetane number | | | 73 |
| ASTM D 5293 | CCS-30, mPas | 1780 | | |
| | CCS-35, mPas | 2920 | 690 | |
| ASTM D 445 | kV40, cSt | 25.7 | 10.9 | 2.4 |
| ASTM D 445 | kV100, cSt | 5.4 | 2.9 | |
| ASTM D 2270 | VI | 153 | 126 | |
| ASTM D 2887 | 0.5%, ° C. | | | 171 |
| | 10%, ° C. | 431 | 355 | 199 |
| | 50%, ° C. | 453 | 384 | 267 |
| | 90%, ° C. | 497 | 415 | 339 |
| | 99.5%, ° C. | | | 361 |
| DIN 51581-2 | GC Noack | 4.4 | 33.1 | |
| FIMS | paraffins | 90.5 | | |
| | mononaphthenes | 9.5 | | |
| | dinaphthenes | 0 | | |
| | other naphthenes | 0 | | |
| EN12916 | Monoaromatics % | | | 0.2 |
| | Diaromatics % | | | <0.1 |
| | Triaromatics % | | | <0.02 |
| ASTM D 3120 | S, mg/kg | 0 | 0 | 1.1 |
| ASTM D 4629 | N, mg/kg | 0 | 0 | <1 |
| ENISO 12205 | Oxidation Stability (g/m3) max | | | 1 |

Example 8

Determination of the Biological Origin of the Hydrocarbon Component

Hydrocarbon component of biological origin was weighed into mineral oil based Group III base oil, and mixed thoroughly. For the first sample, 0.5014 g of the hydrocarbon component of biological origin was weighed, and base oil component of the Group III was added in an amount to obtain a total weight of 10.0000 g; for the second sample, 1.0137 g of the hydrocarbon component of biological origin was weighed, and base oil component of the Group III was added in an amount to obtain a total weight of 10.0232 g. The measured results are summarized in Table 7 below. Content of radioactive carbon ($^{14}C$ isotope) is expressed as "percent modern carbon", based on the content of radioactive carbon of the atmosphere in 1950. At present, the content of radioactive carbon of the atmosphere is about 107%. $\delta^{13}C$ value shows the ratio of stable carbon isotopes $^{13}C/^{12}C$. By means of this value, the isotope fractionation found in our process may be corrected. Actual results are presented in the last column.

TABLE 7

Content of radioactive carbon

| Sample | $^{14}C$ content, % | $\delta^{13}C$ | Bio proportion, % |
|---|---|---|---|
| Mineral oil | 0.1 ± 0.07 | −29.4 | 0 |
| Bio oil | 106.7 ± 0.4 | −28.9 | 100 |
| Mineral + bio, 5% by weight | 5.0 ± 0.3 | −29.3 | 4.60 ± 0.28 |
| Mineral + bio, 10% by weight | 10.8 ± 0.3 | −26.9 | 10.04 ± 0.29 |

Example 8

Carbon Number Distribution

Figure 3:
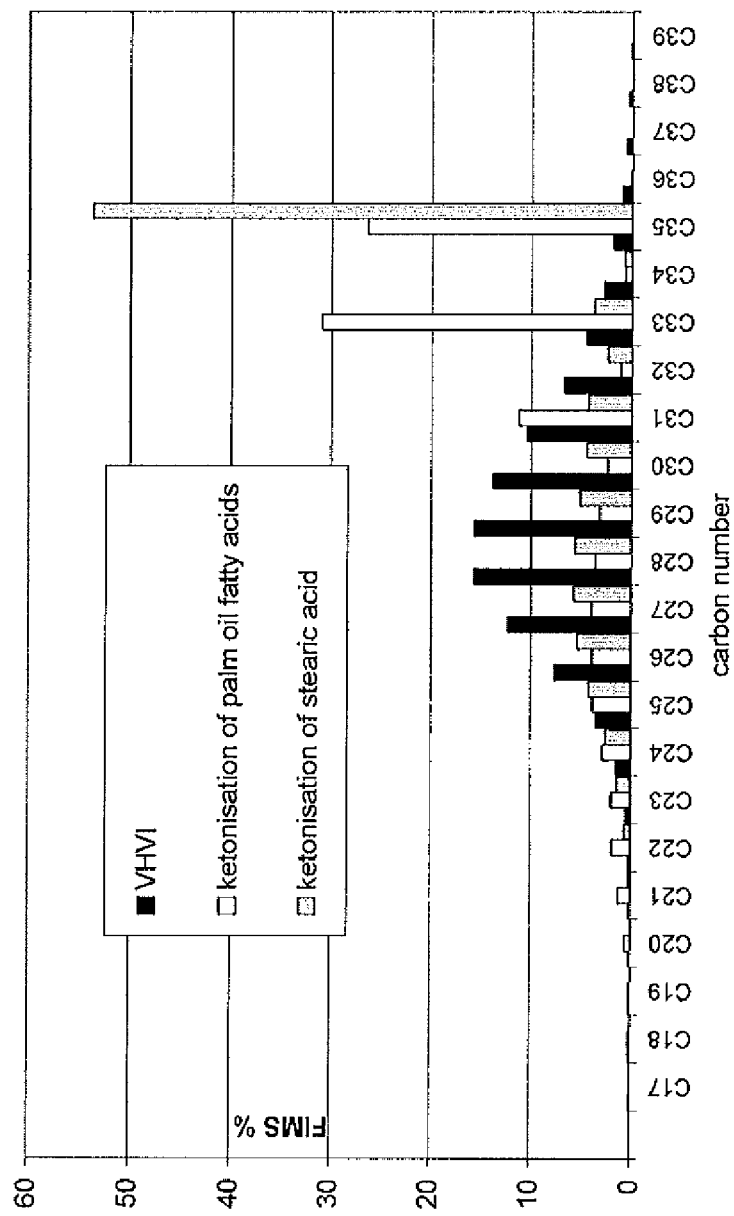
FIG. 3 is a graph showing the carbon number distributions of VHVI (413-520° C. cut) and the baseoils of invention (360° C. cut).

The proportion of hydrocarbons in certain carbon number range of the base oil product is dependent on distillation. In FIG. 3 the carbon number distributions of VHVI (413-520° C. cut) and the baseoils of invention (360-° C. cut) are shown. The carbon number distribution of the base oils according to invention is narrower than that of conventional base oils when distillation is cut in similar manner at >413° C. corresponding to C26 paraffin. In addition to the narrow carbon number distribution, the baseoils of the invention contain also higher amount of higher boiling fractions compared to the conventional product of same viscosity range (KV100 about 4 cSt), as shown in FIG. 3. The lower boiling components with carbon number <C31 are due to cracking in isomerization. The higher boiling compounds enhance VI.

The invention claimed is:

1. A base oil, comprising branched hydrocarbons having carbon numbers of at least $C_{18}$, and at least 90% by weight of saturated hydrocarbons, 5-15% by weight of mononaphthenes and further comprising not more than 1% by weight of fused dinaphthenes and polynaphthenes, and wherein at least 75% by weight of the saturated hydrocarbons have a width of the carbon number range of no more than 9, wherein the kinematic viscosity KV100 is from 3 cSt to 8 cSt, and wherein the low temperature dynamic viscosity CCS-30 is no more than $34.066*(KV100)^{2.3967}$ cP, and wherein the $^{14}C$ isotope content of the total carbon content in the base oil is at least 50% of the $^{14}C$ isotope level in the year 1950, and wherein said base oil is obtained in a process comprising ketonisation, hydrodeoxygenation and isomerization steps, using a feedstock comprising at least one compound selected from the group consisting of triglycerides, carboxylic acids having a carbon number $C_1$-$C_{38}$, esters of $C_1$-$C_{38}$ carboxylic acids with $C_1$-$C_{11}$ alcohols, $C_1$-$C_{38}$ alcohols, $C_1$-$C_{38}$ aldehydes, $C_1$-$C_{38}$ carboxylic acid anhydrides, and metal salts of $C_1$-$C_{38}$ carboxylic acids, esters of $C_1$-$C_{38}$ carboxylic acids with $C_{12}$-$C_{38}$ alcohols, natural waxes, dicarboxylic acids and polyols, and the ketonisation is carried out in the presence of metal oxide catalyst under a pressure from 0 to 10 MPa and at a temperature ranging from 100 to 500° C., the ketonisation product is hydrodeoxygenated in the presence of a hydrodeoxygenation catalyst containing at least one component selected from the group consisting of metals of the Group VIII or Group VIA of the periodic system of the elements and a support, under a hydrogen pressure ranging from 0.1 to 20 MPa at a temperature ranging from 100 to 500° C., and the isomerization is carried out in the presence of a isomerization catalyst containing a metal of the Group VIII of the periodic system of the elements and/or a support, under a hydrogen pressure ranging from 0 to 20 MPa at a temperature ranging from 100 to 500° C.

2. The base oil according to claim 1, wherein the base oil comprises at least 95% by weight of saturated hydrocarbons.

3. The base oil according to claim 1, wherein the base oil comprises at least 97% by weight of saturated hydrocarbons.

4. The base oil according to claim 1, wherein at least 50% by weight of the saturated hydrocarbons have a width of the carbon number range of not more than 7.

5. The base oil according to claim 1, wherein the viscosity index of said base oil is more than 115.

6. The base oil according to claim 1, wherein at least 50% by weight of the saturated hydrocarbons have a width of the carbon number range of not more than 5.

7. The base oil according to claim 1, wherein the viscosity index of said base oil is more than 120.

8. The base oil according to claim 1, wherein the $^{14}C$ isotope content of the total carbon content in the base oil is at least 90% of the $^{14}C$ isotope level in the year 1950.

9. The base oil according to claim 1, wherein the feedstock comprises at least one compound selected from the group consisting of $C_4$-$C_{24}$ fatty acids, $C_4$-$C_{24}$ fatty acid alkyl esters, $C_4$-$C_{24}$ fatty acid metal salts, $C_4$-$C_{24}$ fatty alcohols, $C_4$-$C_{24}$ fatty aldehydes, esters of $C_4$-$C_{24}$ fatty acids with $C_{12}$-$C_{24}$ fatty alcohols and $C_4$-$C_{24}$ fatty acid anhydrides derived from starting material of biological origin, and mixtures thereof.

10. The base oil according to claim 1, wherein said starting material of biological origin is selected from the group consisting of plant fats, plant oils, plant waxes, animal fats, animal oils, animal waxes, fish fats, fish oils, fish waxes, and
 a. free fatty acids or fatty acids obtained by hydrolysis, acid transesterification or pyrolysis reactions from plant fats, plant oils, plant waxes, animal fats, animal oils, animal waxes, fish fats, fish oils, fish waxes, and
 b. esters obtained by transesterification from plant fats, plant oils, plant waxes, animal fats, animal oils, animal waxes, fish fats, fish oils, fish waxes, and
 c. fatty acid alkyl esters obtained by esterification of alcohols with fatty acids of plant, animal and fish origin, and
 d. fatty acid metal salts obtained by saponification of free fatty acids, plant fats, plant oils, plant waxes, animal fats, animal oils, animal waxes, fish fats, fish oils, fish waxes, and
 e. alcohols and aldehydes obtained as reduction or hydrogenolysis products of free fatty acids, or fatty acids from plant fats, plant oils, plant waxes, animal fats, animal oils, animal waxes, fish fats, fish oils, fish waxes, and
 f. fatty alcohols obtained by hydrolysis, transesterification and pyrolysis from waxes of biological origin, and
 g. anhydrides of fatty acids from plant fats, plant oils, plant waxes, animal fats, animal oils, animal waxes, fish fats, fish oils, fish waxes, and h. waste and recycled food grade fats and oils, and fats, oils and waxes obtained by genetic engineering, and
i. mixtures of said materials.

11. The base oil according to claim 1, wherein a hydrocarbon or a mixture of hydrocarbons is added to the feedstock and/or as a diluent to process steps.

12. The base oil according to claim 1, wherein the ketonisation is performed at a pressure from 0.1 to 5 MPa at a temperature ranging from 100 to 400° C.

13. The base oil according to claim 1, wherein the metal oxide catalysts is Na, Mg, K, Ca, Sc, Cr, Mn, Fe, Co, Ni, Cu, Zn, Sr, Y, Zr, Mo, Rh, Cd, Sn, La, Pb, Bi or a rare earth metal oxide catalyst on or without a support.

14. The base oil according to claim 13, wherein the support is laterite, bauxite, titanium dioxide, silica and/or aluminium oxide.

15. The base oil according to claim 1, wherein the hydrodeoxygenation is performed under a hydrogen pressure ranging from 1 to 15 MPa at a temperature ranging from 150 to 400° C.

16. The base oil according to claim 1, wherein the hydrodeoxygenation catalyst contains at least one component selected from the group consisting of Pd, Pt, Ni, NiMo and CoMo metals, and active carbon, alumina and/or silica support.

17. The base oil according to claim 1, wherein after the hydrodeoxygenation, hydroisomerization is carried out under a hydrogen pressure ranging from 1 to 15 MPa at a temperature ranging from 200 to 400° C.

18. The base oil according to claim 1, wherein the catalyst of the hydroisomerization step contains a molecular sieve and a Pd, Pt or Ni metal and/or a support, said support being alumina and/or silica.

19. The base oil according to claim 1, wherein the isomerization is performed before the ketonisation using carboxylic acid or carboxylic acid alkyl ester as feed, at a temperature from 150-350° C. at a pressure of 0-5 MPa in the presence of an isomerization catalyst.

20. The base oil according to claim 19, wherein from 0 to 8% of water or alcohol is added to the feedstock.

21. The base oil according to claim 19, wherein prior to the ketonisation, prehydrogenation is performed under a hydrogen pressure between 0.1 and 20 MPa and at a temperature between 50 and 400° C., in the presence of a catalyst.

22. The base oil according to claim 21, wherein the catalyst contains at least one component selected from the group consisting of metals of the Group VIII and VIA of the periodic system of the elements, and a support.

23. The base oil according to claim 19, wherein from 1 to 3% of water or alcohol is added to the feedstock.

24. The base oil according to claim 19, wherein the prehydrogenation is performed under a hydrogen pressure between 1 and 15 MPa and at a temperature between 100 and 300° C., in the presence of a catalyst.

25. The base oil according to claim 19, wherein the prehydrogenation catalyst is a supported Pd, Pt, Ni, Ru, Rh, NiMo or CoMo catalyst, the support being active carbon, alumina and/or silica.

26. The base oil according to claim 1, wherein the isomerization is carried out in the presence of an acidic catalyst.

27. The base oil according to claim 1, wherein the metal oxide is molybdenum, manganese and/or magnesium oxide.

28. The base oil according to claim 1, wherein the isomerization is performed before the ketonisation at a temperature from 200 to 290° C. and at a pressure of 0.1-2 MPa in the presence of an isomerization catalyst.

29. The base oil according to claim 1, wherein the isomerization is carried out in the presence of a catalyst being a zeolite of the pentasil or mordenite type.

30. The base oil according to claim 1, wherein the base oil contains less than 0.5% of polycyclic naphthenes measured by FIMS.

31. The base oil according to claim 1, wherein the base oil contains less than 0.1% of polycyclic naphthenes measured by FIMS.

32. A base oil comprising branched hydrocarbons having carbon numbers of at least $C_{18}$, and at least 90% by weight of saturated hydrocarbons, 5-15% by weight of mononaphthenes and wherein fused dinaphthenes and polynaphthenes are in a concentration of not more than 1% by weight, and wherein at least 50% by weight of the saturated hydrocarbons have a width of the carbon number range of no more than 9, wherein the kinematic viscosity KV100 is from 3 cSt to 8 cSt, and wherein the low temperature dynamic viscosity CCS-30 is no more than $34.066*(KV100)^{2.3967}$ cP, and the distillation range of the base oil being no more than 70° C., and said base oil is obtained in a process comprising ketonisation, hydrodeoxygenation and isomerization steps, using a feedstock comprising at least one compound selected from the group consisting of triglycerides, carboxylic acids having a carbon number $C_1$-$C_{38}$, esters of $C_1$-$C_{38}$ carboxylic acids with $C_1$-$C_{11}$ alcohols, $C_1$-$C_{38}$ alcohols, $C_1$-$C_{38}$ aldehydes, $C_1$-$C_{38}$ carboxylic acid anhydrides, and metal salts of $C_1$-$C_{38}$ carboxylic acids, esters of $C_1$-$C_{38}$ carboxylic acids with $C_{12}$-$C_{38}$ alcohols, natural waxes, dicarboxylic acids and polyols, and the ketonisation is carried out in the presence of metal oxide catalyst under a pressure from 0 to 10 MPa and at a temperature ranging from 100 to 500° C., the ketonisation product is hydrodeoxygenated in the presence of a hydrodeoxygenation catalyst containing at least one component selected from the group consisting of metals of the Group VIII or Group VIA of the periodic system of the elements and a support, under a hydrogen pressure ranging from 0.1 to 20 MPa at a temperature ranging from 100 to 500° C., and the isomerization is carried out in the presence of a isomerization catalyst containing a metal of the Group VIII of the periodic system of the elements and/or a support, under a hydrogen pressure ranging from 0 to 20 MPa at a temperature ranging from 100 to 500° C.

33. The base oil according to claim 32, wherein the base oil contains less than 0.5% of polycyclic naphthenes measured by FIMS.

34. The base oil according to claim 32, wherein the base oil contains less than 0.1% of polycyclic naphthenes measured by FIMS.

35. A base oil comprising branched hydrocarbons having carbon numbers of at least $C_{18}$, and at least 90% by weight of saturated hydrocarbons, 5-15% by weight of mononaphthenes and wherein fused dinaphthenes and polynaphthenes are in a concentration of not more than 1% by weight, and wherein at least 50% by weight of the saturated hydrocarbons have a width of the carbon number range of no more than 5, wherein the kinematic viscosity KV100 is from 3 cSt to 8 cSt, and wherein the low temperature dynamic viscosity CCS-30 is no more than $34.066*(KV100)^{2.3967}$ cP, and the distillation range of the base oil being no more than 70° C., and said base oil is obtained in a process comprising ketonisation, hydrodeoxygenation and isomerization steps, using a feedstock comprising at least one compound selected from the group consisting of triglycerides, carboxylic acids having a carbon number $C_1$-$C_{38}$, esters of $C_1$-$C_{38}$ carboxylic acids with $C_1$-$C_{11}$ alcohols, $C_1$-$C_{38}$ alcohols, $C_1$-$C_{38}$ aldehydes, $C_1$-$C_{38}$ carboxylic acid anhydrides, and metal salts of $C_1$-$C_{38}$ carboxylic acids, esters of $C_1$-$C_{38}$ carboxylic acids with $C_{12}$-$C_{38}$ alcohols, natural waxes, dicarboxylic acids and polyols, and the ketonisation is carried out in the presence of metal oxide catalyst under a pressure from 0 to 10 MPa and at a temperature ranging from 100 to 500° C., the ketonisation product is hydrodeoxygenated in the presence of a hydrodeoxygenation catalyst containing at least one component selected from the group consisting of metals of the Group VIII or Group VIA of the periodic system of the elements and a support, under a hydrogen pressure ranging from 0.1 to 20 MPa at a temperature ranging from 100 to 500° C., and the isomerization is carried out in the presence of a isomerization catalyst containing a metal of the Group VIII of the periodic system of the elements and/or a support, under a hydrogen pressure ranging from 0 to 20 MPa at a temperature ranging from 100 to 500° C.

36. A base oil, comprising branched hydrocarbons having carbon numbers of at least $C_{18}$, and at least 90% by weight of saturated hydrocarbons, 5-15% by weight of mononaphthenes and further comprising not more than 1% by weight of fused dinaphthenes and polynaphthenes, and wherein at least 75% by weight of the saturated hydrocarbons have a width of the carbon number range of no more than 9, wherein the kinematic viscosity KV100 is from 3 cSt to 8 cSt, and wherein the low temperature dynamic viscosity 1 CCS-30 is no more than $34.066*(KV100)^{2.3967}$ cP, and wherein said base oil is obtained in a process comprising ketonisation, hydrodeoxygenation and isomerization steps, using a feedstock comprising at least one compound selected from the group consisting of triglycerides, carboxylic acids having a carbon number $C_1$-$C_{38}$, esters of $C_1$-$C_{38}$ carboxylic acids with $C_1$-$C_{11}$ alcohols, $C_1$-$C_{38}$ alcohols, $C_1$-$C_{38}$ aldehydes, $C_1$-$C_{38}$ carboxylic acid anhydrides, and metal salts of $C_1$-$C_{38}$ carboxylic acids, esters of $C_1$-$C_{38}$ carboxylic acids with $C_{12}$-$C_{38}$ alcohols, natural waxes, dicarboxylic acids and polyols, and the ketonisation is carried out in the presence of metal oxide catalyst under a pressure from 0 to 10 MPa and at a temperature ranging from 100 to 500° C., the ketonisation product is hydrodeoxygenated in the presence of a hydrodeoxygenation catalyst containing at least one component selected from the group consisting of metals of the Group VIII or Group VIA of the periodic system of the elements and a support, under a hydrogen pressure ranging from 0.1 to 20 MPa at a temperature ranging from 100 to 500° C., and the isomerization is carried out in the presence of a isomerization catalyst containing a metal of the Group VIII of the periodic system of the elements and/or a support, under a hydrogen pressure ranging from 0 to 20 MPa at a temperature ranging from 100 to 500° C.

37. A base oil, comprising branched hydrocarbons having carbon numbers of at least $C_{18}$, and at least 90% by weight of saturated hydrocarbons, 5-15% by weight of mononaphthenes and further comprising not more than 1% by weight of fused dinaphthenes and polynaphthenes, and wherein at least 75% by weight of the saturated hydrocarbons have a width of the carbon number range of no more than 9, wherein the kinematic viscosity KV100 is from 3 cSt to 8 cSt, and wherein the low temperature dynamic viscosity CCS-30 is no more than $34.066*(KV100)^{2.3967}$ cP, and wherein the $^{14}C$ isotope content of the total carbon content in the base oil is at least 50% of the $^{14}C$ isotope level in the year 1950.

* * * * *